United States Patent
Kambara et al.

(10) Patent No.: US 6,821,734 B2
(45) Date of Patent: Nov. 23, 2004

(54) METHOD FOR TESTING NUCLEIC ACID SEQUENCE

(75) Inventors: Hideki Kambara, Hachioji (JP); Guohua Zhou, Nanjing (CN); Kazunori Okano, Shiki (JP); Keiichi Nagai, Higashiyamatoshi (JP)

(73) Assignee: Hitachi, Ltd., Tokyo (JP)

( * ) Notice: Subject to any disclaimer, the term of this patent is extended or adjusted under 35 U.S.C. 154(b) by 206 days.

(21) Appl. No.: 10/083,340

(22) Filed: Feb. 27, 2002

(65) Prior Publication Data

US 2003/0124544 A1 Jul. 3, 2003

(30) Foreign Application Priority Data

Oct. 30, 2001 (JP) ...................................... 2001-331853

(51) Int. Cl.[7] ........................... C12Q 1/68; C12P 19/34; C07H 21/02
(52) U.S. Cl. ...................... 435/6; 435/91.2; 435/91.21; 536/23.1; 536/24.3; 536/24.31; 536/24.33

(56) References Cited

U.S. PATENT DOCUMENTS 6,027,889 A * 2/2000 Barany et al. ............... 435/6

FOREIGN PATENT DOCUMENTS

WO     WO 98/28440    * 7/1998

OTHER PUBLICATIONS

Pamela M. Holland, Richard D. Abramson, Robert Watson and David H. Gelfand, "Detection of specific polymerase chain reaction product by utilizing the 5'→3' exonuclease activity of Thermus aquaticus DNA polymerase", Proc. Natl Acad. Sci, vol. 88, pp. 7276–7280, Aug. 1991, Biochemistry.

Victor Lyamichev, Andrea L. Mast, Jeff G. Hall, James R. Prudent, Michael W. Kaiser, Tsetska Takova, Robert W. Kwiatkowski, Tamara J. Sander, Monika de Arruda, David A. Arco, Bruce P. Neri, and Mary Ann D. Brow, "Polymorphism identification and quantitative detection of genomic DNA by invasive cleavage of oligonucleotide probes", Nature Biotechnology, vol. 17, Mar. 1999, pp. 292–296.

(List continued on next page.)

Primary Examiner—Jeffrey Fredman
(74) Attorney, Agent, or Firm—Reed Smith LLP; Stanley P. Fisher, Esq.; Juan Carlos A. Marquez, Esq.

(57) ABSTRACT

A method for examining nucleotide sequences of a sample includes adding a group of primers of multiple species to a solution containing the sample and simultaneously synthesizing complementary strands at each of the multiple regions containing the nucleotide sequences; designing the DNA probes with specific sequences elongate the complementary strands by the presence or absence of mutations in the nucleotide sequences, wherein the same number of such DNA probes and the nucleotide sequences are used for complementary strand synthesis; using the nucleotide sequences or their complementary sequences as a template to convert pyrophosphate produced during the elongation reaction to ATP which then reacts with chemiluminescent substrates to develop luminescence to be detected. According to the method, sensitivity is greatly increased by amplification of the amount of pyrophosphate produced in synthesis of the complementary strands without amplifying the copies of nucleotide sequences.

17 Claims, 24 Drawing Sheets

OTHER PUBLICATIONS

Masato Orita, Youichi Suzuki, Takao Sekiya, and Kenshi Hayashi, "Rapid and Sensitive Detection of Point Mutations and DNA Polymorphisms Using the Polymerase Chain Reaction", Oncogene Division, National Cancer Center Research Institute, Apr. 24, 1989, pp. 874–879.

Jian–Bing Fan, Xiapoqiong Chen, Marc K, Halushka, Anthony Berno, Xiohua Huang, Thomas Ryder, Robert J. Lipshutz, David J. Lockhart and Aravinda Chakravarti, "Parallel Genotyping of Human SNPs Using Generic High–density Oligonucleotide Tag Arrays", Genome Research Letter, pp. 853–860.

David R. Walt, "Bead–based Fiber–Optic Arrays", Science, vol. 287, Jan. 21, 2000, pp. 451–452.

Afshin Ahmadian, Baback Gharizadeh, Anna C. Gustafsson, Fredrik Sterky, Pal Nyren, Mathias Uhlen and Joakin Lundeberg, "Single–Nucleotide Polymorphism Analysis by Pyrosequencing", Analytical Biochemistry 280, (2000) pp. 103–110.

Guo–hua Zhou, Masao Kamahori, Kazunori Okano, Gao Chuan, Kunio Harada and Hideki Kambara, "Quantitative detection of single nucleotide polymorphisms for a pooled sample by a bioluminometric assay coupled with modified primer extension reactions (BAMPER)", Nucleic Acids Research, 2001, vol. 29, No. 19e93, pp. 1–11.

Joseph Sambrook and David W. Russell, "Molecular Cloning, a Laboratory Manual", Third Edition, Cold Spring Harbor Laboratory Press.

Tsugunori Notomi, Hiroto Okayama, Harumi Masubuchi, Toshihiro Yonekawa, Keiko Watanabe, Nobuyuki Amino and Tetsue Hase, "Loop–mediated isothermal amplification of DNA", Nucleic Acids Research, 2000, vol. 28, No. 12, pp. i–vii.

* cited by examiner

REACTION OF COMPLEMENTARY STRAND SYSTHESIS

SEQUENCE LISTING

```
<160> NUMBER OF SEQ ID NOS: 4

<210> SEQ ID NO 1
<211> LENGTH: 95
<212> TYPE: DNA
<213> ORGANISM: Artificial Sequence
<220> FEATURE:
<223> OTHER INFORMATION: Sequence of portion of model gene including
      mutation.

<400> SEQUENCE: 1
ctttcttgcg gagattctct tcctctgtgc gccggtctct cccaggacag gcacaaacac     60
gcacctcaaa gctgttccgt cccagtagat tacca                                95

<210> SEQ ID NO 2
<211> LENGTH: 22
<212> TYPE: DNA
<213> ORGANISM: Artificial Sequence
<220> FEATURE:
<223> OTHER INFORMATION: DNA probe for detecting wild type and having
      an artificial mismatched base at the third base from the 3'end.

<400> SEQUENCE: 2
aacagctttg aggtgcgtga ta                                              22

<210> SEQ ID NO 3
<211> LENGTH: 22
<212> TYPE: DNA
<213> ORGANISM: Artificial Sequence
<220> FEATURE:
<223> OTHER INFORMATION: DNA probe for detecting mutation type and
      having an artificial mismatched base at the third base from the
      3'end.

<400> SEQUENCE: 3
aacagctttg aggtgcgtga tt                                              22

<210> SEQ ID NO 4
<211> LENGTH: 22
<212> TYPE: DNA
<213> ORGANISM: Artificial Sequence
<220> FEATURE:
<223> OTHER INFORMATION: Sequence portion of SEQ.No.1 which is a target
      sequence hybridized with DNA probe having base sequence of
      SEQ.No.2 or No.3.
```

```
<400> SEQUENCE: 4
aaacacgcac ctcaaagctg tt                                          22
```

METHOD FOR TESTING NUCLEIC ACID SEQUENCE

BACKGROUND OF THE INVENTION

This invention relates to a method for examining nucleotide sequences for DNA tests and genetic diagnosis, and specifically to a method for simultaneous examination of multiple mutations contained in the genome DNA.

With recent development of human genome projects, the relation between disease- or drug-sensitivity and genes is being elucidated. It has been clarified that the genes related to disease- or drug-sensitivity do not operate solely but several genes function in combination with each other. Single-nucleotide polymorphism (SNP) in the human genome has been documented to occur once per 1000 bases and to be related to individual's constitution, drug sensitivity and resistance to diseases, and the relation between loci of SNPs and these phenomena is being elucidated. Genetic diagnosis for actual diseases and consultation based on genetic information are now starting, and rapid development of a method for examining SNPs in multiple genomic sites efficiently and at low cost is essential.

Under these conditions, various analytical methods have been proposed; (a) Taqman assay, detecting an increase in fluorescent intensity accompanied by degradation of marker probes during PCR amplification (Ref. 1: Proc. Natl. Acad. Sci. USA: 88, 7276–7280 (1991)), (b) Invader assay, detecting fluorescence caused by degradation of fluorescence-labeled probes, for which formation of triple-strand DNA and an enzyme recognizing mismatch are combined (Ref. 2: Nature Biotech.: 17, 292–296 (1999)), (c) single-strand conformation polymorphism (SSCP), detecting the difference in electrophoretic mobility of DNA with or without mutations by gel electrophoresis (Ref. 3: Genomics: 5, 874–879 (1989)), and (d) DNA chips, or DNA probe arrays in which probes are immobilized to surface of a plane (Ref. 4: Genomics Res.: 10, 853–860 (2000)), and (e) a method in which DNA probes are immobilized to colorcoded beads and these are collected to be used as probe arrays (Ref. 5: Science: 287, 451–452 (2000)). All these five methods utilize detection of fluorescence by laser excitation. In addition, several other methods such as pyrosequencing using chemiluminescence (Ref. 6: Anal. Biochem.: 280, 103–110 (2000)) have been reported.

Since any of the above-mentioned methods does not satisfy all the basic points such as low running costs, simple and brief operation and high reliability, a new method has been greatly desired. Inventors and others have already proposed a convenient and low-cost detection method for DNA mutations (bioluminometric assay with modified primer extension reaction, BAMPER) (Ref. 7: Nucl. Acid Res.: 29, e93 (2001)) and have obtained excellent results. However, this method also has several problems; amplification of the copy number of DNA by PCR is necessary in prior to each measurement, and sample preparation is necessary for every subject of examination.

In detection of chemiluminescence, pyrophosphate is reacted with APS and converted to ATP, which then reacts with luciferin to produce chemiluminescence. Although chemiluminescence is believed to have a high sensitivity, the normal detection limit for the number of DNA copies is only in the order of femtomole (fmol) because APS that converts pyrophosphate to ATP can also react with luciferin. For this reason, amplification of target DNA is essential in prior to examination.

On the other hand, examination of multiple test sites has been desired in clinical diagnosis related to diseases. For this purpose, multiple test sites should be amplified. However, amplifying every test site one by one is not realistic because of its high cost. DNA probe arrays (DNA chips) recently used for analysis of genetic expression profiles are known to be suitable for examining multiple target regions, but it is difficult to recognize one-base mutation since the method involves hybridization of targets and probes. A new method solving these problems is desired.

Most of the methods that have been developed so far or are currently used require amplification of the copy number and/or sample preparation for every test subject, which often causes problems of handiness, time and cost especially for the subjects with many test sites.

SUMMARY OF THE INVENTION

The purpose of this invention is to provide a method for examining nucleotide sequences, including an efficient and low-cost method for preparing samples with many test sites, based on a method utilizing chemiluminescence, for which low-priced equipment and test reagents are available.

To solve the above problems, this invention discloses a means, comprising;

a sample solution containing multiple targets (DNA fragments) subjected to examination is equally added to multiple subcells set in a reaction vessel. The sequences designed to hybridize with different targets are used to hybridize different DNA probes and targets in each of the subcells. Under the conditions in which the solution in the subcells is not mixed, complementary strand synthesis and chemiluminescence resulting from pyrophosphate are induced to examine SNPs at any of the test sites easily.

The invention also discloses a method, comprising;

following the synthesis of strands complementary to subject DNA fragments by using anchor primers, all of the DNA fragments are PCR-amplified en bloc using a pair of universal primers common to all the DNA fragments. Complementary DNA strands including test sites are synthesized en bloc by means of the anchor primers, and complementary strand synthesis is repeatedly conducted in the subcells by using PCR products of the DNA fragments and the complementary DNA strands including test sites. With these procedures, more pyrophosphate is produced and reacted with chemiluminescent reagents so that multiple mutations in DNA can be detected simultaneously with optically high sensitivity. Furthermore, the invention discloses a method for producing a large amount of pyrophosphate, a chemiluminescent substance, by using DNA strands specifically prepared for signal amplification in addition to target DNA.

In a process of the invention, detection of target DNA contained in subject DNA, especially detection of one-base mutation, is achieved by detecting chemiluminescence induced by the reaction of ATP and luciferin/luciferase; ATP is made from pyrophosphate that is produced in the course of synthesis of complementary DNA strands. For higher detection sensitivity, the reaction system is constructed so that a large chain of reactions of complementary strand synthesis is triggered when targets are present in a sample and acts as a template for synthesis of complementary strands. This process of the invention has achieved four to five orders of magnitude of high sensitivity compared to the prior process, pyrosequencing, which has been known as a method for examining genetic mutations by chemiluminescence. With this process, only several hundreds of copies of DNA are enough for detection. In addition, many reaction cells are prepared in a reaction vessel to make it possible to examine multiple test sites simultaneously.

In a process of the invention, the above problems are solved by the following steps; after simultaneous amplification, target regions are hybridized with probes immobilized to different cells that are separated from each other in a reaction vessel, which is followed by complementary strand synthesis. A large amount of pyrophosphate is thus produced in each cell, where chemiluminescent reaction is performed separately. In more detail, initiation of complementary strand synthesis depends on the presence of single-base mutation when synthesis of complementary strands is performed in each cell by using a target DNA strand as a template. If the DNA contains mutations, complementary strand synthesis is allowed to be induced. The complementary strands thus acts as a trigger for the subsequent synthesis of complementary strands. A great amount of pyrophosphate is finally produced, which makes is possible to examine the presence of target DNA and the status of mutations at high sensitivity.

Representative compositions of the invention are described as follows. In the first composition of the invention, a group of primers consisting of multiple primer species is added to a solution containing a sample subjected to examination. Simultaneous synthesis of complementary strands is performed at each of the multiple regions containing target nucleotide sequences to be examined. DNA probes with specific sequences are designed so that elongation of complementary strands is affected by the presence or absence of mutations in the target nucleotide sequences. The same number of such DNA probes and the target sequences is used for elongation of complementary strands. Elongation reaction of complementary strands using the targets or the sequences complementary to the targets as a template and the following reaction, in which pyrophosphate produced during the elongation reaction is converted to ATP and reacted with chemiluminescent substrates to develop luminescence, are performed in the subcells of the reaction vessel that are compartmentalized for each said target. By detecting the luminescence, mutations present in the target nucleotide sequences are detected.

In the second composition of the invention, a group of probes consisting of multiple probe species is added to a sample solution subjected to examination. Two probes are hybridized to each of the different target sequences. The DNA probes are prepared so that the binding reaction of the two probes in ligation is affected by the presence of base mutations in DNA subjected to examination. Using a group of the probes consisting of pairs of these probes, long DNA strands are prepared by ligation reaction of the two probes. Furthermore, synthesis of complementary strands is performed at least once in subcells of a reaction vessel by using either the DNA strands or their complementary strands as a template. Pyrophosphate, the product of complementary DNA synthesis in each of the subcells, is converted to ATP and reacted with chemiluminescent substrates to develop luminescence in the subcells compartmentalized for each of the target sequences. With these processes, mutations in genes or DNA can be identified by detection of luminescence.

In the third composition of the invention, the primers with a common sequence at their 5' termini can regulate synthetic reaction of complementary strands, where the target DNA strands are used as a template, depending on the presence or absence of mutations. Following the complementary strand synthesis using the primers, pyrophosphate is produced during synthesis of complementary strands using either the DNA strands obtained by amplification of the product of the complementary strand synthesis or their complementary strands. Pyrophosphate is converted to ATP, which is subsequently used for chemiluminescence. The presence of DNA mutations or the presence of target DNA is determined by luminescent intensity.

In the forth composition of the invention, using genomes or multiple target DNA as a template, multiple species of the first probes are hybridized to the templates in a single reaction vessel to prepare multiple species of the first complementary strands by the first synthesis of complementary strands. Then excess of the first probes are isolated and removed from the first complementary strands. With the first complementary strands as a template, the second synthesis of complementary strands is performed using multiple species of the second probes to obtain the second complementary strands, which partially contains the same sequence as that of said target DNA. In each compartmentalized area sorted with species of said first complementary strands, pyrophosphate is produced in the synthesis of the second complementary strands or in the complementary strand synthesis using said second complementary strands as a template, and is converted to ATP, which develops chemiluminescence for detection. With these processes, specific sequences and mutations in base sequences of the target DNA are detected.

In according to the representative compositions of the invention, a large amount of pyrophosphate (PPi) can be produced, which makes it possible to examine the presence of target DNA and the status of mutation at high sensitivity.

Other objects, features and advantages of the invention will become apparent from the following description of the embodiments of the invention taken in conjunction with the accompanying drawings.

DESCRIPTION OF THE EMBODIMENTS

This invention is described below by showing examples for a genetic test as an example of a method for examining nucleotide sequences. First, a genetic test and a mutation test based on BAMPER method are described for better understanding. In examinations using DNA probes, DNA chips and other techniques are used, where targets are hybridized to probes for fluorescent detection. However, it is often difficult to distinguish between a mutant and a wild type by difference in hybridization ability resulting from single-base mutation. In this case, the hybridized probes are used as a primer to perform complementary strand synthesis to distinguish the above difference.

For example, primers are designed so that the 3' terminus is located immediately before a mutation site, and fluorescence-labeled dNTP is added to the probes. And then mass spectrometry (in this case, fluorescent label is not essential), gel electro-phoresis and capture by DNA probe arrays are performed to detect mutations by fluorescence.

In addition, a series of methods monitoring the production of pyrophosphate during complementary strand synthesis by chemiluminescence is noted as a convenient method. One of these methods using chemiluminescence is BAMPER method proposed by the inventors and others. The 3' terminus of DNA probes is placed exactly at a mutation site in target DNA. It is widely known that, when the 3' terminus of the primers used for complementary strand synthesis is complementary to a target sequence and thus completely hybridized to the target, synthesis of complementary strands is appropriately induced. However, when the 3' terminus is not complementary to the target, the synthesis does not or seldom occur.

In other words, synthesis of complementary strands depends on, or is switched by, agreement or disagreement between the 3' terminus of the primers and the target sequences, i.e., whether the 3' terminus is complementary to the target or not. When substituting a base species near the 3' terminus by a different one that is not complementary to the target, hybridization at the 3' terminal region of the primer becomes weaker. If the 3' terminus is complementary to the target, synthesis of complementary strands is induced as usual, but if it is not complementary, the terminus is almost unstuck from the target and no synthesis occurs. BAMPER method makes use of such primers with an artificial mismatch near to the 3' terminus, and detects chemiluminescence by ATP converted from pyrophosphate that is produced by the synthesis of complementary strands using these primers.

Figure 26:
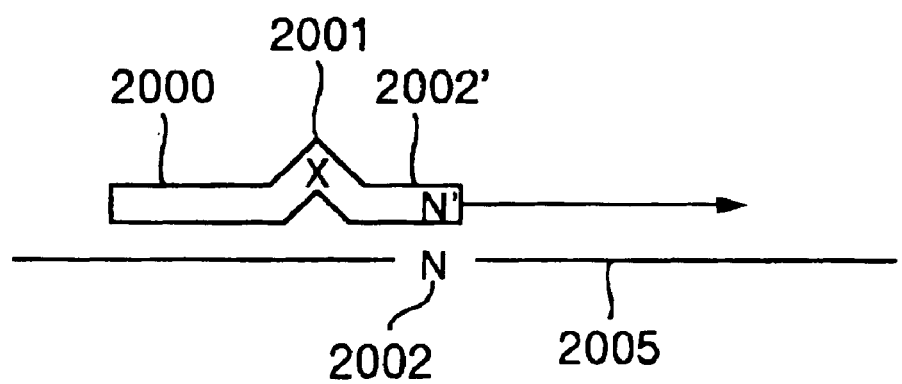
FIG. 26 is an example of an artificial mismatch probe in the prior art, BAMPER method.

FIG. 26 illustrates an example of an artificial mismatch probe used in BAMPER method. A primer 2000 is hybridized to a sample DNA 2005. When the 3' terminus of the primer 2002' is complementary to the sample DNA 2002, elongation reaction 2003 is induced. Whether the elongation is initiated or not is determined by complementarity between the sample DNA 2002 and the primer 2002', which makes it possible to examine SNPs in N. In this example, an artificial mismatch is introduced to the locus 2001 in the primer.

Since the amount of pyrophosphate is proportional to the length of the DNA strand synthesized by complementary synthesis, higher sensitivity of almost two orders of magnitude is expected compared to pyrosequencing, in which pyrophosphate is produced when one base is used for elongation of complementary strands in the synthesis. However, the copy number of DNA used for examining mutations contained in the genome is approximately $10^3$–$10^5$. Provided that 100-base elongation is achieved by synthesis of complementary strands, the number of pyrophosphate produced would be $10^5$–$10^7$, which is insufficient for direct detection. Therefore, amplification of DNA copies is carried out by PCR as the first step.

Two probes, each of which is complementary to either a mutant or a wild type, are independently used as a probe (primer) for reactions to distinguish a mutant and a wild type correctly. By comparing the luminescent intensities produced in the reactions, the presence and types (homozygous/heterozygous) of mutations are judged. An outline of the reactions related to pyrophosphate production accompanied by complementary strand synthesis and to chemiluminescence is shown below. Details are described in Ref. 6. In the following diagram, –(X)→indicates an enzyme X coexisting in the reaction.

ssDNA+primer+dNTP–(polymerase)→ssDNA+primer–(dNTP)$_n$+ nPPi

PPi+APS–(ATPsulfurylase)→ATP+SO$_4^{2-}$

ATP+luciferin+O$_2$–(luciferase)→AMP+PPi+oxyluciferin+CO$_2$+hv dNTP–(ATPase)→dNDP+Pi–(ADPase)→dNMP+Pi ATP–(ATPase)→ADP+Pi–(ADPase)→AMP+Pi

EXAMPLE 1

Figure 1:
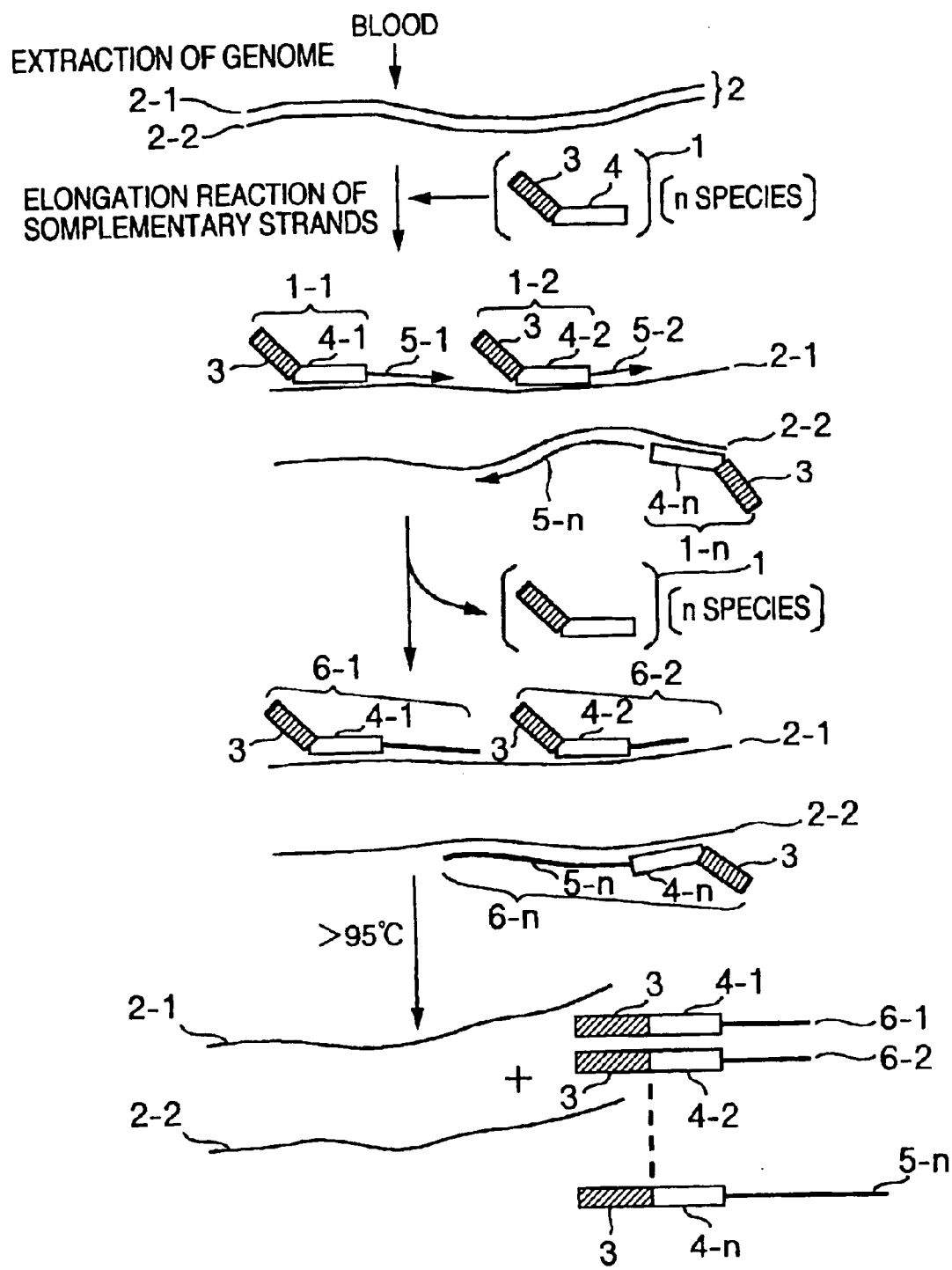
FIG. 1 is method for simultaneous preparation of the DNA fragments containing multiple SNP regions in example 1 of the genetic test of the invention.
Figure 2:
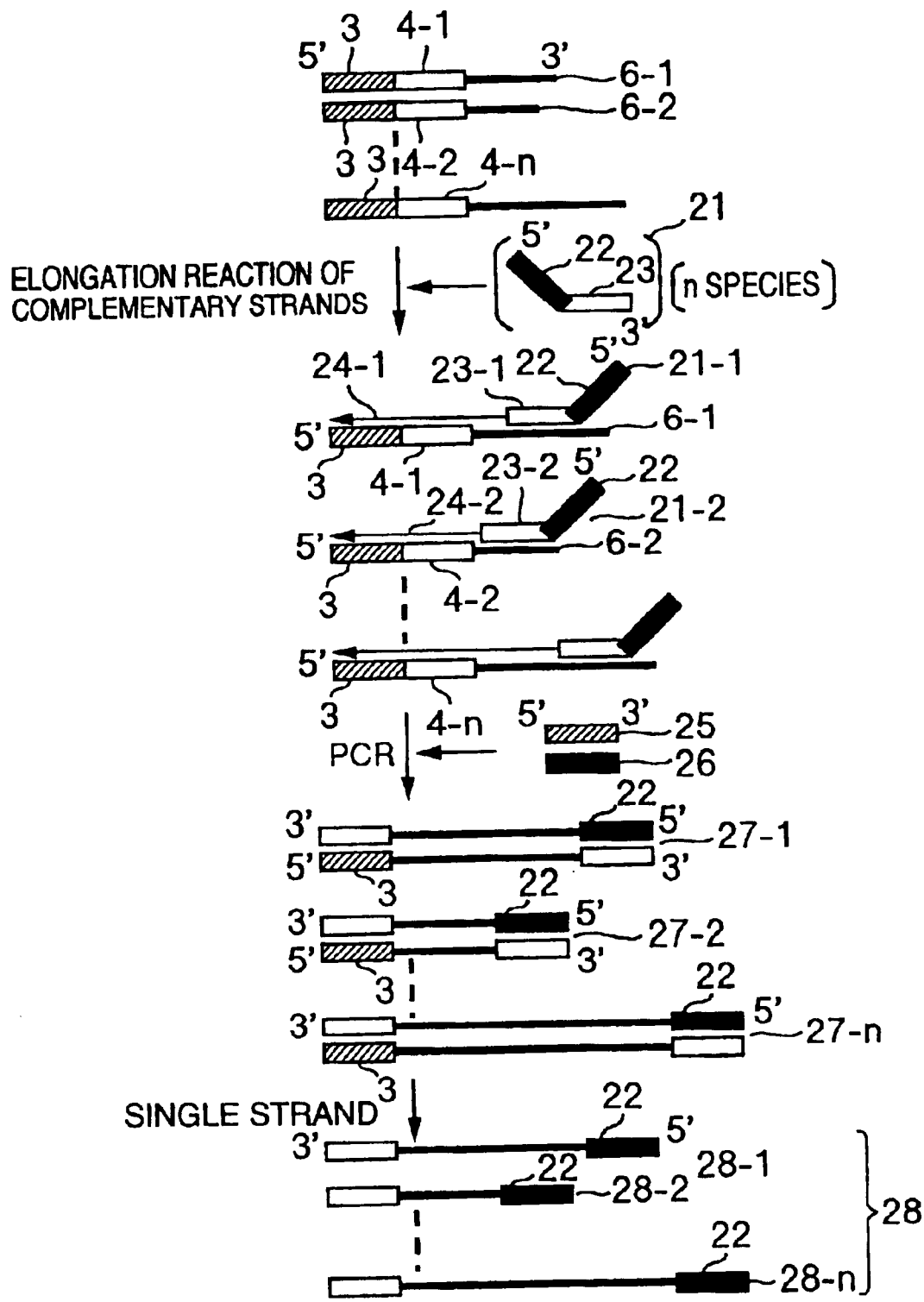
FIG. 2 is method for simultaneous preparation of the DNA fragments containing multiple SNP regions in example 1 of the genetic test of the invention (following FIG. 1).
Figure 3:
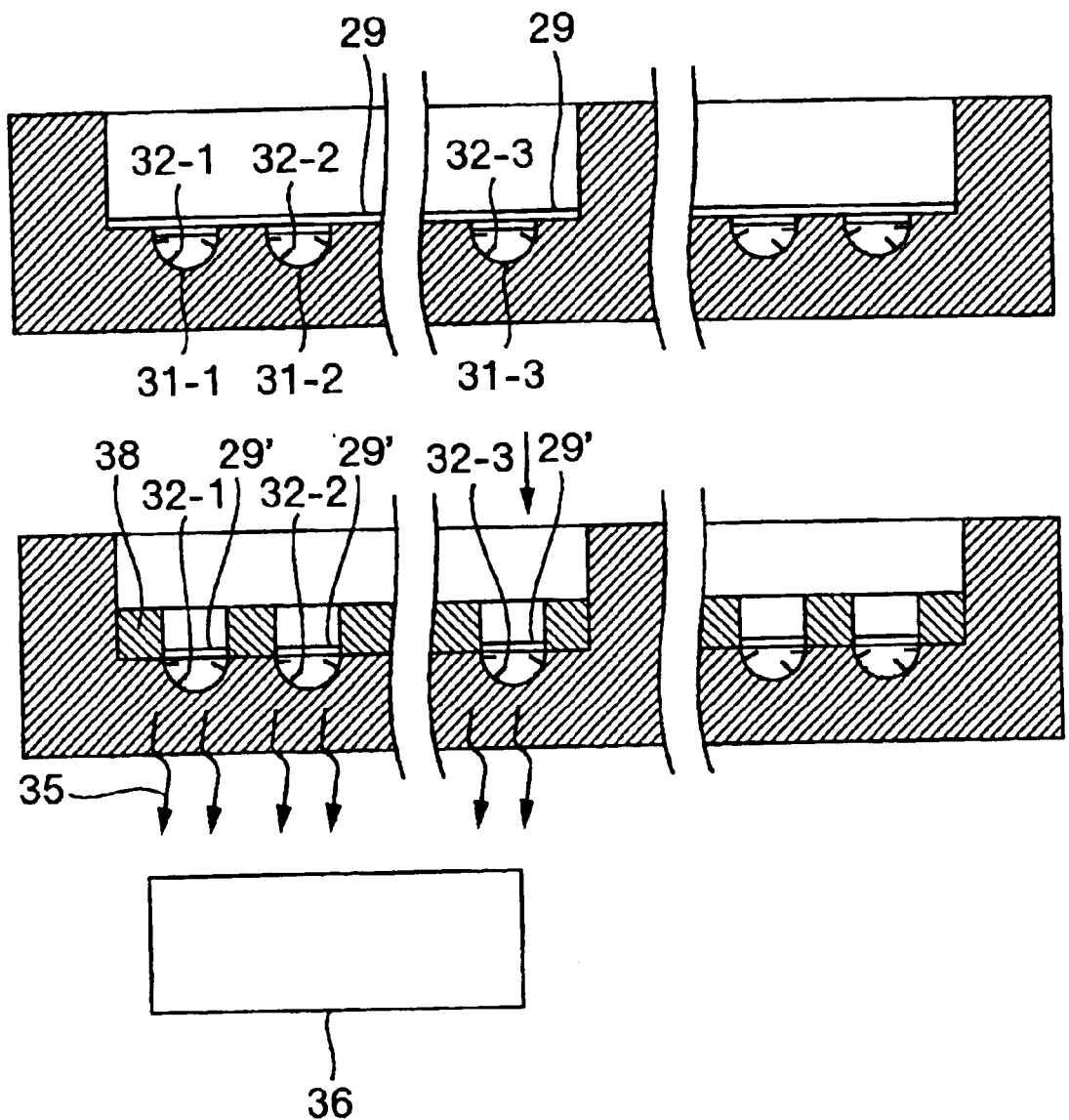
FIG. 3 is reaction vessels and a detection device used in example 1 of the genetic test of the invention.

Outlines of a method for a genetic test (a method for examining nucleotide sequences) are shown in FIGS. 1–3. FIG. 1 explains a method for simultaneous preparation of DNA fragments containing multiple SNP regions in example 1 of the genetic test of the invention. FIG. 2 follows FIG. 1 and explains a method for simultaneous preparation of DNA fragments containing multiple SNP regions in example 1 of the genetic test of the invention. FIG. 3 demonstrates a reaction vessel and a detecting device used in example 1 of the genetic test of the invention.

In example 1, multiple SNPs are examined using the genome 2 as a sample. The following discussion can be applied to the cases in which a target is mRNA or cDNA. The genome is extracted from blood in according to the method described in the literature (Ref. 8: Molecular Cloning Third Edition, Cold Spring Harbor Laboratory Press: pp 6.8–6.11 (2001)). Commercially available DNA extraction equipment and extraction kit could be used for this process. A probe 1 is prepared so that it contains an anchor that can be hybridized to the 3'-terminal region near the SNPs subjected to examination. The number of the probes should be equal to that of the SNPs. "Probe 1" indicates the whole set of multiple probes with the anchor in the following explanations. Therefore, an anchor probe 1 includes multiple primers, 1-1, 1-2, . . . 1-n, each of which contains a variable sequence (an arbitrary sequence region) 4 and an anchor sequence 3. The anchor sequence 3 is not hybridized with single-strand targets, 2-1 and 2-2, and is common to all of the probe 1. The strand complementary to the anchor 3 sequence will be used later.

The probe 1 at final concentration of 0.25 μM is hybridized (annealed at 55° C. for 1 mm) to the genome, which has been previously denatured at 95° C. for 30 sec, and the first synthesis of complementary strands is carried out at 72° C. for 3 mm. The complementary strand regions elongated in this first synthesis are shown by 5-1, 5-2, . . . 5-n. Although various species of primers coexist, any of the byproducts that block the reaction is not produced because the reaction is not repeated as in the case of PCR. Excess of the primer 1 was removed by washing immediately after the synthesis of complementary strands. The primers elongated by the synthesis, 6-1, 6-2, . . . 6-n, are maintained with being hybridized to the genome 2-1 and 2-2. The elongated primers, 6-1, 6-2, . . . 6-n, are then isolated from the genome by increasing the temperature of the solution up to 95–100° C. and collected. A group of DNA fragments (complementary strand-1; 6-1, 6-2, . . . 6-n) of various sequences that contain the subject DNA regions and an anchor sequence at their 5' termini are thus obtained.

An anchor primer 21 (final concentration, 0.25 μM) is prepared; the primer can hybridize with the 3'-terminal region next to the SNPs in the complementary strand-1 subjected to examination. The anchor primer 21 is a mixture of 21-1, 21-2, . . . 21-n. The primer consists of an arbitrary sequence region 23 and an anchor sequence 22 that is not hybridized to a group of the DNA fragments (complementary strand-1), 6-1, 6-2, . . . 6-n, and is common to the entire group of the DNA fragment (complementary strand-1). The anchor primer 21 is hybridized to the mixture of complementary strands, 6-1, 6-2, . . . 6-n, prepared in FIG. 1, and the complementary strand synthesis 24 (the synthesis of the second complementary strands, 24-1, 24-2, . . . 24-n) is performed.

After removing the primer 21, the primer 25 (final concentration, 0.2 μM) having the same sequence as that of the anchor sequence 3 of the primer 1 and the primer 26 (final concentration, 1 μM) having the same sequence as that of the anchor sequence 22 of the primer 21 are added to the solution containing the product of the complementary strand synthesis 24 to perform PCR amplification. The conditions of the PCR are as follows; the solution consists of 0.25 μM of MgCl.sub.2, .times.10 PCR buffer of the commercial kit and 0.0625 units/μL of Taq DNA polymerase. The cycle consisting of denaturation at 95° C. for 30 sec, annealing at 55° C. for 30 sec and elongation at 72° C. for 1 mm is repeated 35 times, and then the reaction mixture is incubated at 72° C. for 5 mm so that the elongation reaction of the product is completed. There is a possibility that the primers 1 and 21 competitively inhibit the PCR by the primers 25 and 26. To remove the primer 21 effectively and prevent the inhibition, biotin is conjugated to the 5' terminus of the primer 1, and the product of the complementary strand synthesis is collected by means of avidin-labeled magnetic beads. Otherwise, the primer 21 is not necessarily removed if the concentrations of the primers 25 and 26 are higher than that of the primer 21. When performing the PCR using 10 μL of a sample under these conditions, several dozens fmol of single-strand DNA are obtained.

Both of the primers 25 and 26 are hybridize to the anchor sequence of all the DNA strands with the same efficacy. Thus, homogeneous amplification of DNA strands is achieved regardless of the variation of sequence of target fragments. Single-strand DNA is obtained by asymmetry PCR, in which the concentration of one of the primers 25 and 26 is set higher than the other as in the above condition, and by labeling one of the primers 25 and 26 with biotin to be captured by avidin-labeled magnetic beads after the complementary strand synthesis. The single-strand DNA 28 (28-1, 28-2, . . . 28-n) thus obtained is subjected to a test. The single-strand DNA 28 includes the anchor sequence 22 at the 5' terminus and the sequence complementary to the anchor sequence 3 at the 3' terminus.

Figure 4:
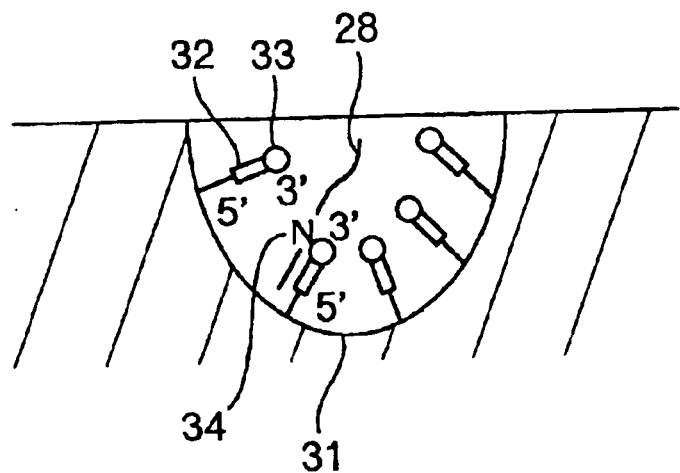
FIG. 4 is DNA probes immobilized to the reaction vessel for detecting SNPs in example 1 of the genetic test of the invention.

The solution 29 containing the single-strand DNA sample 28 thus obtained is added to a reaction vessel shown in FIG. 3. Although only one reaction vessel is shown in FIG. 3, the vessel corresponds to a single well (6 mm in diameter) of a microtiter plate in actual experiments. In each well of the reaction vessel are smaller subcells, 31-1, 31-2, . . . 31-n, to each of which different species of DNA probes, 32-1, 32-2, . . . 32-n, are immobilized. As shown in FIG. 4, a DNA oligomer containing the primer sequence 32 whose 3' terminus has been designed to hybridize to a mutation site N34 of the sample DNA 28 is immobilized to each subcell 31.

Shortly, multiple subcells are set in each of the wells on a microtiter plate, and different probes are separately immobilized to each subcell.

Figure 5:
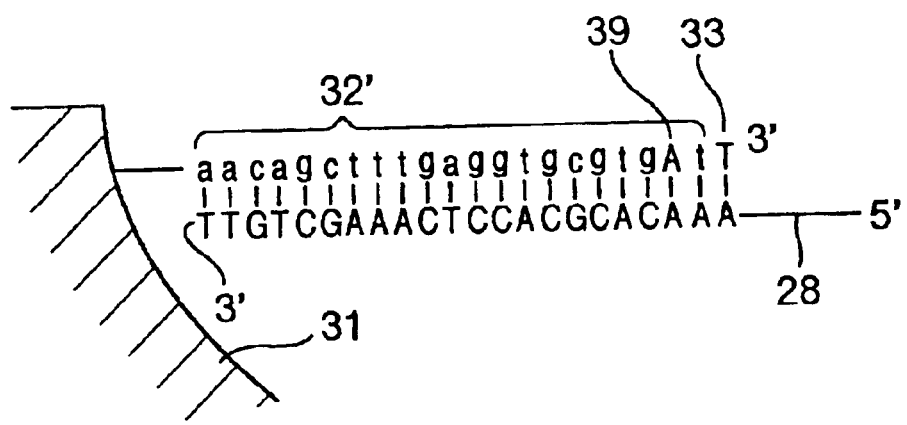
FIG. 5 is a model of hybridization of the SNP-containing DNA fragments to the DNA probes in example 1 of the genetic test of the invention.

FIG. 4 illustrates the DNA probes immobilized to a reaction vessel for detecting SNPs in example 1 of the genetic test of the invention. FIG. 5 shows a model in which the DNA fragment containing SNP is hybridized with the DNA probe in example 1 of the genetic test of the invention. The structure of the DNA probe 32 is shown in FIGS. 4 and 5. The probe 32 consists of the region 32' that is hybridized specifically with the target 28 and the region 33 that recognizes mutation. Sequence 1 shows a subject sequence containing a mutation site in the target DNA 28 as a model gene.

```
Sequence 1
5'-CTTTCTTGCGGAGATTCTCTTCCTCTGTGCGCCGGTCTCTCCCAGG
ACAGGCACAAACACGCACCTCAAAGCTGTTCCGTCCCAGTAGATTACCA
-3'
```

The sequences of the probe 32 corresponding to the sequence 1 are the sequence 2 and the sequence 3.

```
Sequence 2
5'-aacagctttgaggtgcgtgAtA-3'

Sequence 3
5'-aacagctttgaggtgcgtgAtT-3'
```

In these sequences, A and T at the 3' terminus of the sequences 2 and 3, respectively, are the mutation-recognizing sites; the primer with A corresponds to the wild type, and that with T, to the mutant. The base A, 39, at the third position from the 3' terminus indicates that an artificial mismatch has been introduced. The sequence 4 of the single-strand DNA 28 containing the sequence 1 binds complementarily to the probe sequence possessing the sequence 2 or the sequence 3.

```
Sequence 4
5'-AAACACGCACCTCAAAGCTGTT-3'
```

When adding sufficient amount of the solution 29 (10 μL), a subcell is fulfilled and some portion of the solution is overflowed. DNA is diffused and then hybridized to the probes in subcells. Each of the different species of the DNA is separately captured by each of the subcells. Since the solution is overflowed and thus can freely move among the subcells, effective hybridization is accomplished. After sufficient hybridization and removal of excess of the solution 29, the target DNA are sorted with probe species and captured in each subcell. Next, the reaction solution containing DNA polymerase and dNTP that is necessary to the complementary strand is added to the reaction vessel, and the synthetic reaction 51 (FIG. 6) is initiated. On this occasion, the reaction solution in each subcell should not be mixed with each other.

Figure 6:
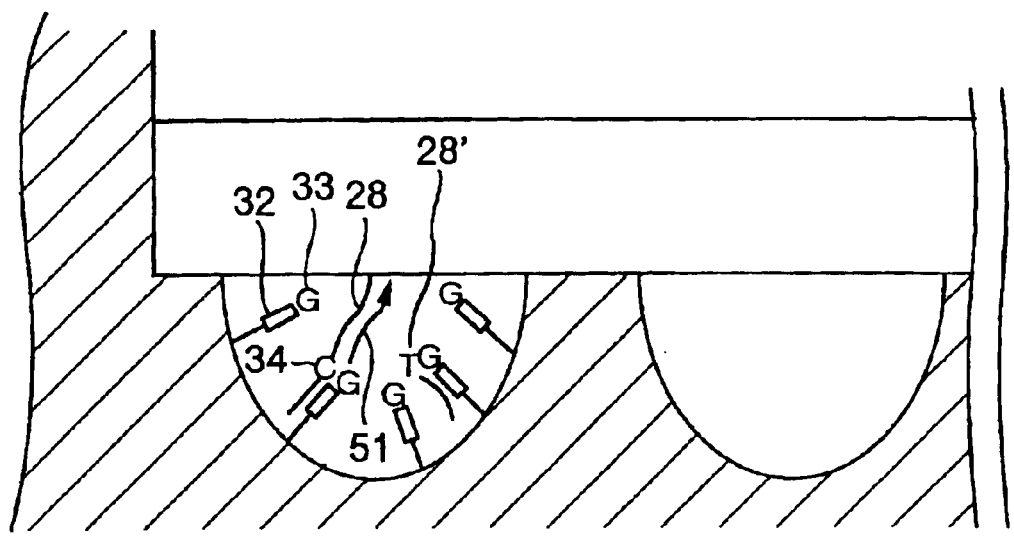
FIG. 6 is specific elongation reaction of complementary strands occurring after the SNP-containing DNA fragments is hybridized with the DNA probes for detecting SNPs that are immobilized to the reaction vessel in example 1 of the genetic test of the invention.

FIG. 6 demonstrates that the DNA fragments containing SNPs are hybridized with the DNA probes for detecting SNPs, and that the specific elongation reaction of complementary strands occurs in example 1 of the genetic test of the invention. As shown in FIG. 6, the complementary strand synthesis is induced for the sample 28 whose sequence corresponds to the 3' terminus of the probe, as indicated by 51. However, the synthesis of complementary strands does not proceed or hardly proceeds for the sample 28', which is not complementary to the probe. With these procedures, the presence of base mutation corresponding to the 3' terminus of the probe can be detected in the sample DNA 28. Two species of probes are usually immobilized to two separate subcells; the 3' terminus of one probe is complementary to the mutant, and the other, to the wild type. Synthesis of complementary strands is performed in each cell, and pyrophosphate produced is converted to ATP, which is subsequently reacted with chemiluminescent reagents. Intensities of induced luminescence are compared to each other. In more detail, the mixture consisting of the recognition primer (1.25 μM), Taq DNA polymerase (0.05 units/μL), $MgCl_2$ (0.15 mM) and dNTP (0.125 mM) is added to each subcell. Pyrophosphate is obtained by five PCR cycles, each of which comprises 94° C. for 10 sec, 50° C. for 10 sec and 72° C. for 20 sec. Pyrophosphate purified by the method described in Ref. 7 Nucl. Acid Res.: 29, e93 (2001) is used for developing chemiluminescence. The above conditions are used in the PCR in the following examples. Detection of pyrophosphate is according to the method described in Ref. 7 Nucl. Acid Res.: 29, e93 (2001).

In example 1, the entire steps comprise; (1) the step, in which the DNA fragments with the sequence complementary to the anchor primer 21 are prepared from various DNA fragments obtained in the complementary strand synthesis using the anchor primer 1, (2) the step, in which the entire DNA fragments are homogeneously amplified using the primers 25 and 26 that possess a sequence identical to the anchor sequence, and (3) the step, in which individual DNA fragments thus obtained are added to the reaction cells, where chemiluminescent reaction is performed (chemiluminescent step).

In the chemiluminescent step, the DNA fragments obtained by PCR and other techniques are divided into different subcells and are captured by the probes immobilized to the surface of each subcell. With these means, complementary strands to different DNA fragments are synthesized in a mutation-specific manner in subcells. Pyrophosphate is produced by the synthesis, converted to ATP, and reacted with chemiluminescent reagents to develop chemiluminescence. SNPs are examined by detecting this chemiluminescence. Among dNTP (N=A, C, G, T) used in synthesis of complementary strands, dATP is substituted with dATPαS, an analog of dATP, since dATP could react with luciferin.

Figure 7:
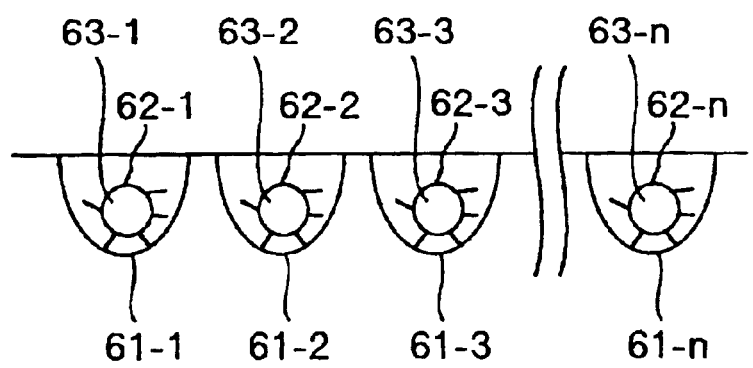
FIG. 7 is an example in which a single bead is used in the reaction vessel in example 1 of the genetic test of the invention.
Figure 8:
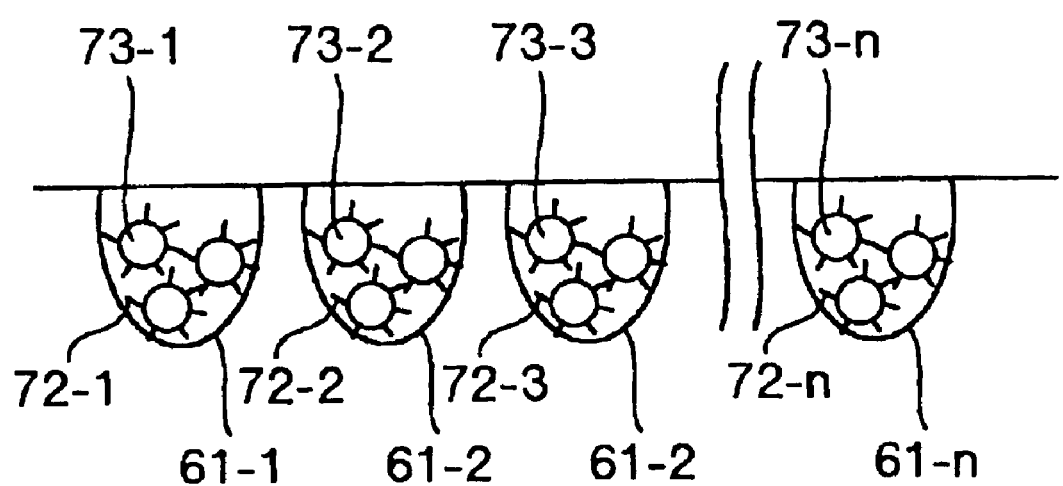
FIG. 8 is an example in which multiple beads are used in the reaction vessel in example 1 of the genetic test of the invention.

As shown in FIGS. 6–8, several methods are available for capturing target DNA in each subcell. The first method is the method illustrated in FIGS. 3–6, in which target-specific probes are immobilized to the surface of subcells, and the targets are captured in each subcell by hybridization. The volume of each subcell is approximately 1 μL; the solution containing DNA fragments is overflowed from the subcells. As a result, the solutions in the subcells are mixed with the outer solution, which makes it possible to perform hybridization effectively and to capture the targets separately into different subcells.

The second method to capture targets with being sorted to species is shown in FIG. 7. In this method, the bead 63 immobilizing the probe 62 is placed in each subcell 61, and the targets are hybridized to the surface of the beads 63. Immobilization of probes to beads is easier than that to subcells. FIG. 7 shows an example, in which a single bead is placed in each cell, but multiple beads 73 could be placed in each cell as shown in FIG. 8. In the example in FIG. 8, the surface area to which probes 72 are immobilized is increased, and therefore this method takes advantage that more targets can be specifically captured in subcells 61.

After the capture of the DNA in subcells, the solution 29 is removed from the reaction vessel, and reagents for complementary strand synthesis and those for chemiluminescence are added to the subcells. To prevent moving of the reaction solution 29', partitioning plates as shown in FIG. 3 could be used to separate each subcell. Otherwise, the solution should be added so that it is not overflowed. The developed luminescence 35 is monitored by a photosensor from either the top or the bottom of the transparent reaction vessel.

As a photosensor, photo-multipliers or photocells that are placed in an array and are adhered to the reaction cells are recommended. Otherwise, CCD imaging using lenses could be possible. Although the reaction is initiated after capturing the target by immobilized specific probes in this example, the primers specific to the target sequences could be dissolved in the solution containing glycerol and polysaccharides, and dried in subcells, so that the reagents including the primers could be stabilized by polysaccharides as matrix for storage. With the primers stored with matrix in this way, target-specific reaction of complementary strand synthesis could be performed by adding the solution containing a set of DNA fragments into each subcell. In this case, extra DNA fragments coexist with the DNA fragments corresponding to each probe, but this does not cause any problem in target detection because the probes have been designed to be highly specific. However, the concentrated targets are divided into many subcells, and therefore amplification step for targets should be performed sufficiently.

The synthetic reaction of complementary strands cannot operate efficiently until the reagents such as primers, which have been trapped in matrix, are dissolved into the reaction solution. It is recommended that the melting temperature of matrix is set at 45–50° C. and that the temperature is increased in prior to the initiation of the reaction, so that partial reaction could be prevented during the process in which DNA is added to each cell.

EXAMPLE 2

Figure 9:
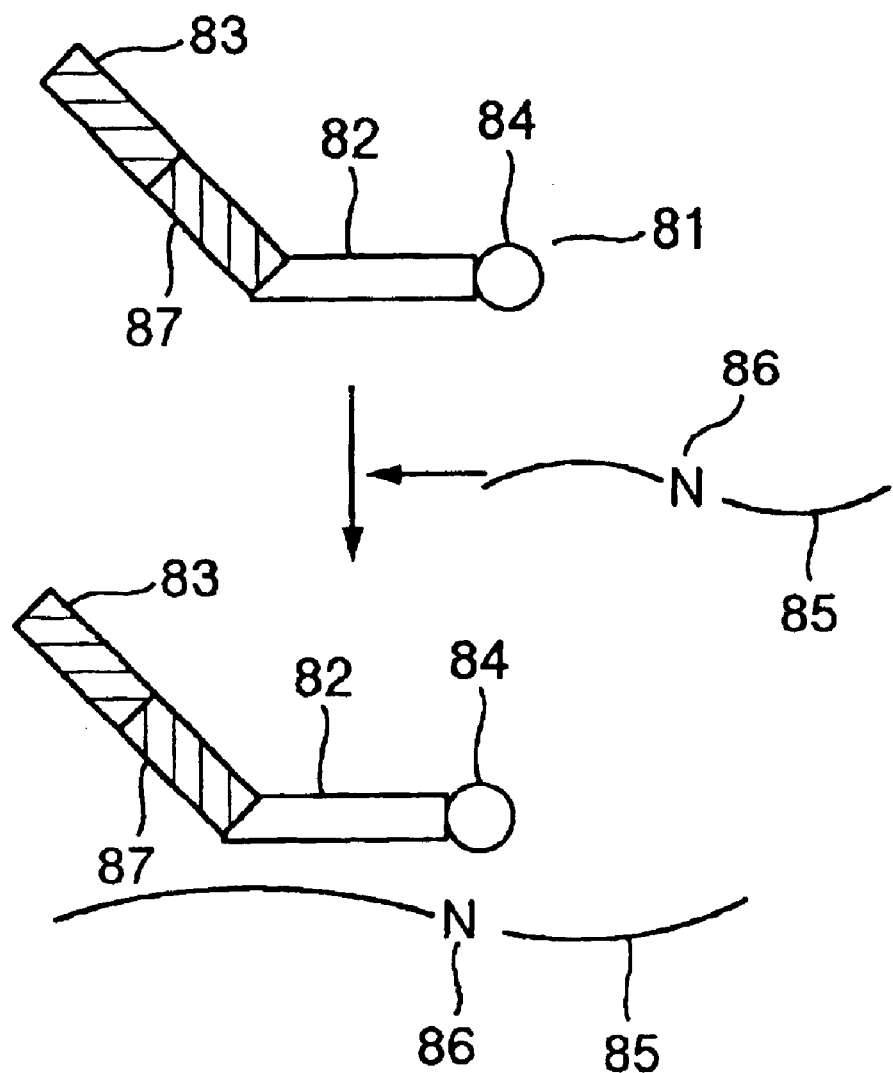
FIG. 9 is construction of the primer used in example 2 of the genetic test of the invention.

In example 1, the anchor primers are used for initiation of the synthesis of complementary strands without recognizing mutations in the targets. In example 2, primers that can recognize mutations are used in the first or the second synthesis of complementary strands in example 1. FIG. 9 indicates the construction of the primers used in example 2 of the genetic test of the invention. The first primer 81, which consists of multiple primers corresponding to different targets, contains the sequence 82 that is complementary to the target and the universal sequence 83 that is not hybridized with the target. The primer 81 is designed so that the 3' terminus 84 is located exactly at the mutated point 86 during hybridization. The same number of the primer 81 as that of mutations is prepared.

Figures 10, 11:
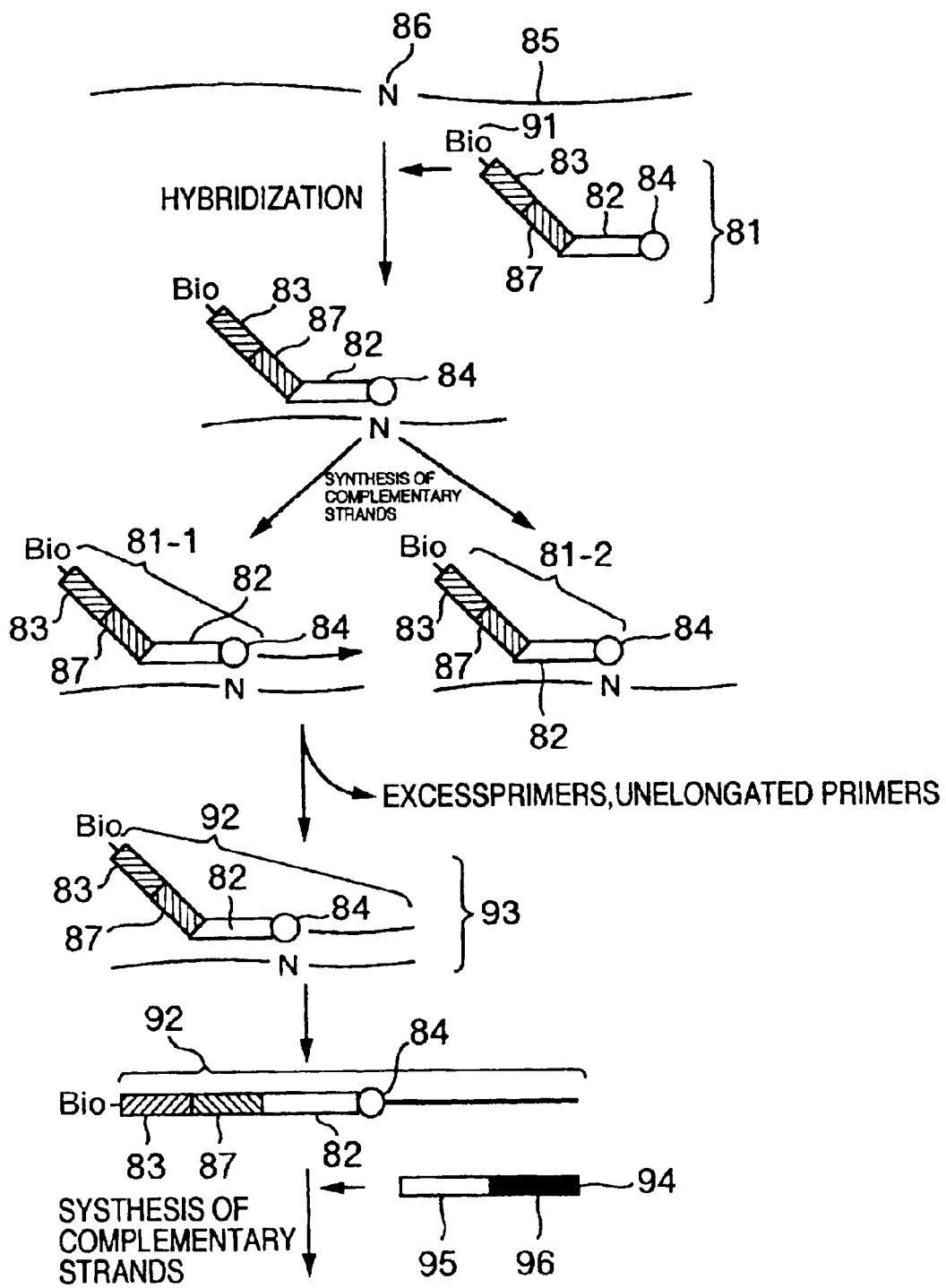
FIG. 10 is recognition of SNPs in example 2 of the genetic test of the invention.
FIG. 11 is capture of the DNA fragments by the probes immobilized to the reaction vessel and release of pyrophosphate produced during elongation of the DNA probes after recognition of SNPs in example 2 of the genetic test of the invention (following FIG. 10).
Figure 11:
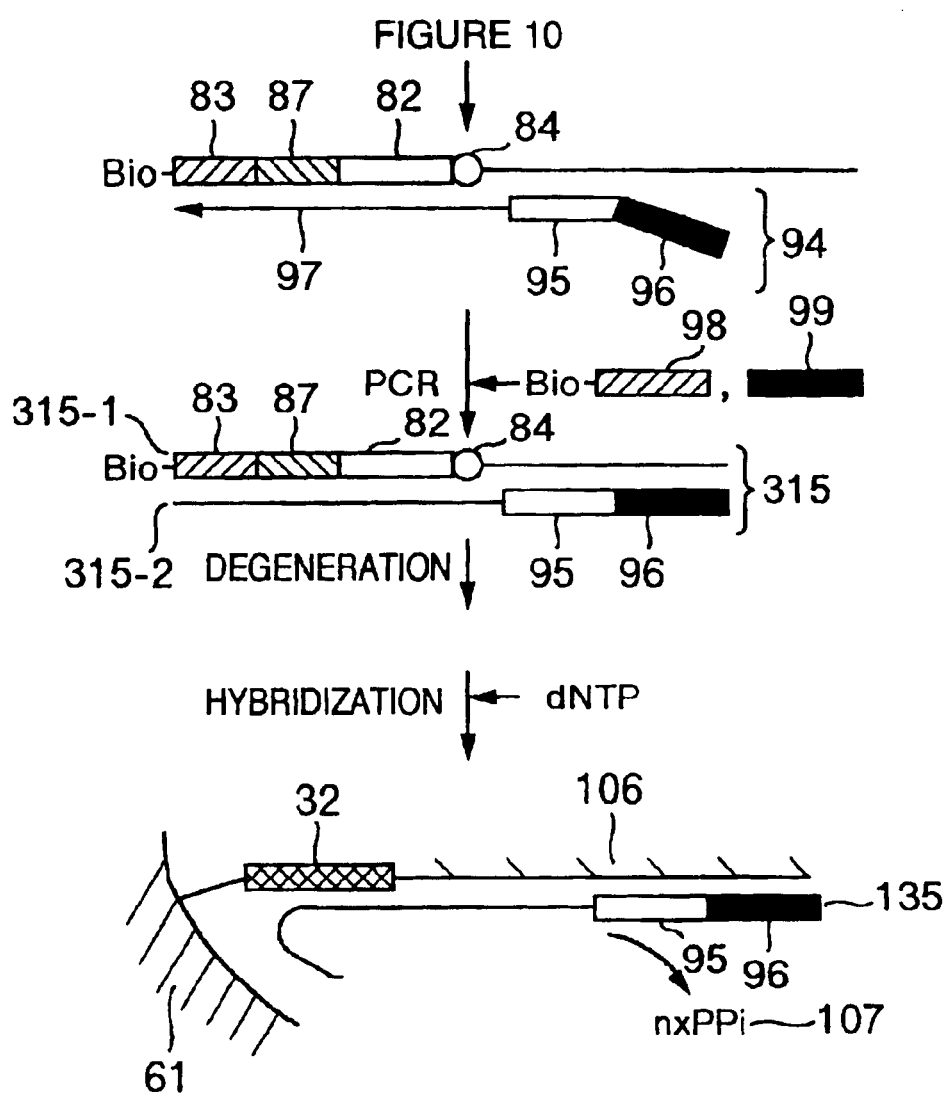
Figure 12:
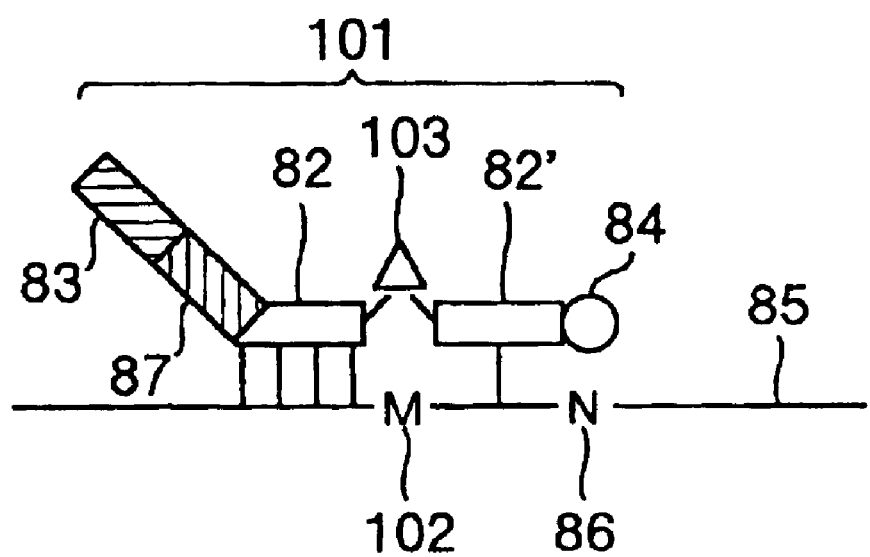
FIG. 12 is construction of the primer used for detecting SNPs in example 2 of the genetic test of the invention.

Two primers, each of which corresponds to a wild type and a mutant, are prepared for each of the test sites for normal SNPs. These primers possess the universal sequence (anchor sequence 83) that is not hybridized with the target. The anchor sequence 83 is used as a priming region for amplification of DNA fragments by PCR or other methods in later steps. In addition, the sequence 87 to recognize mutations is introduced between the universal sequence 83 and the target-specific sequence 82 to detect mutations. FIGS. 10 and 11 show the construction of the primer 81 and the reaction steps including synthesis of complementary strands.

FIG. 10 illustrates how SNPs are discriminated in example 2 of the genetic test of the invention. FIG. 11 follows FIG. 10 and demonstrates that DNA fragments are captured by the probes immobilized to the reaction vessel and that pyrophosphate is released when specific DNA probes are elongated by recognizing SNPs. The primer 81 is hybridized with the target DNA 85 (genome, mRNA, or cDNA). In this example, biotin 91 is conjugated to the 5' terminus of the primer 81. Among the probes 81 that have been hybridized, the probe 81-1 whose 3' terminus completely matches with the target (i.e., the 3' terminus of the primer is complementary to the target) is elongated by complementary strand synthesis, while the primer 81-2 whose 3' terminus does not match with the target (i.e., the 3' terminus of the primer is not complementary to the target) is not elongated.

Thus, the synthesis of complementary strands can be switched over in response to the presence or absence of mutations in the target. To make this nature clearer, an artificial mismatch 103, corresponding to the sequence 102 of the target 85, could be introduced to the region near to the 3' terminus of the primer. The partial sequences 82 and 82' are complementary to the target 85.

After the synthesis of complementary strands (the synthesis of the first complementary strand), unreacted and excess primers are removed. The complementary strand 92 that has an elongated strand of the primer 81 by the complementary strand synthesis remains as the form 93 that is hybridized to the target such as the genome. Next, the complementary strand 92 is released from the target by increasing the temperature to 95–100° C. The primer 94, consisting of the same number of the primers as that of the target species, that can hybridize with the elongated region of the complementary strand 92 is added to perform the synthesis of complementary strands (the synthesis of the second complementary strand), which produces the complementary strand 97.

The primer 94 consists of the target-specific (complementary) region 95 and the universal region (the anchor sequence 96) common to the entire primers 94. The complementary strand (elongated strand) 97 comprises a variety of strands according to target species, but the sequences of the both termini of 97 are invariable; the complementary strand (elongated strand) 97 possesses the primer sequence 94 at the 5' terminus and the sequence complementary to the primer 81 at the 3' terminus.

The primer 98 with the sequence identical to the anchor sequence 83 and the primer 99 with that identical to the anchor sequence 96 are used for PCR amplification. The PCR product 315 (including the DNA strands 315-1 and 315-2) thus obtained is denatured to make the single-strand DNA 315-2, which is subsequently added to the reaction vessel to hybridize with the probe 32 in the subcell 61. By adding dNTPs (dATPαS, dGTP, dCTP, dTTP), the synthesis of complementary strands 106 is performed. Pyrophosphate PPi 107 produced in this reaction is converted to ATP, which is then reacted with luciferin to develop chemiluminescence. The following steps are the same as in example 1.

The probes that discriminate each target could be used in this example. By using the primer having the sequence identical to the target sequence 87, wild types and mutants are distinguished and captured by different subcells, where luminescent reaction is conducted. If the device in which the primer with the target sequence 87 is immobilized to the subcells is prepared on this occasion, the device would be useful for various genetic tests with some improvement in the primer sequence 1 (such as the primer 81 shown in FIGS. 9 and 10).

EXAMPLE 3

In example 2, pyrophosphate is produced by the synthesis of complementary strands using the DNA probes maintained in subcells and the DNA strands containing a target sequence as a template. Pyrophosphate is converted to ATP, which is used for chemiluminescent reaction. Example 3 is an example, in which the DNA strands containing the sequence that is not related to the target sequence are used as a template for the synthesis of complementary strands, by which more pyrophosphate is produced to increase the signal intensity.

Figure 13:
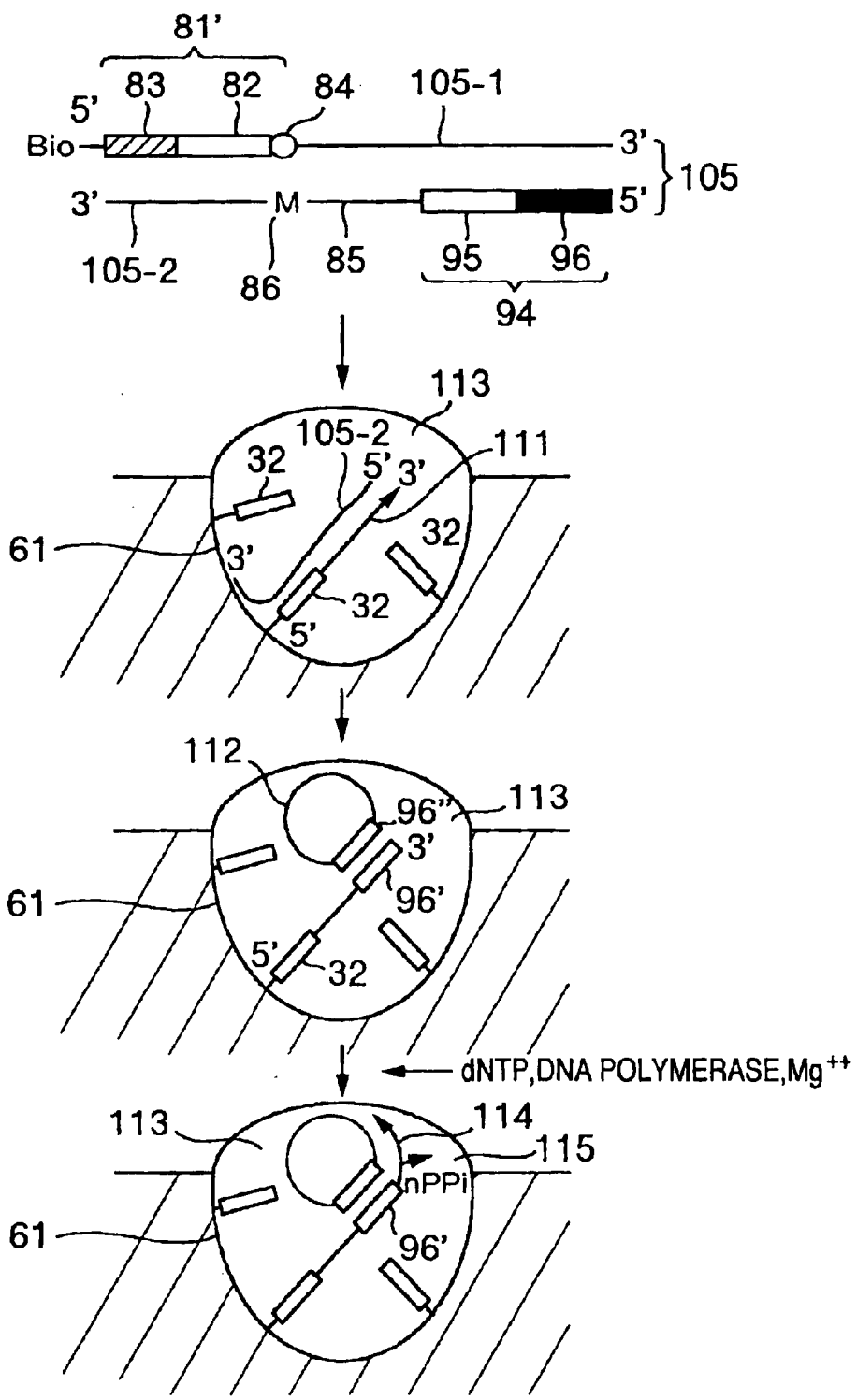
FIG. 13 is an example in which a large amount of pyrophosphate is produced by the reaction of complementary strand synthesis using the DNA fragment containing the sequence that is not related to the target in example 3 of the genetic test of the invention.

FIG. 13 shows an example, in which a large amount of pyrophosphate is produced by elongation reaction of complementary strands using the DNA strands with the sequence that is not the target sequence in example 3 of the genetic test of the invention. In practical 3, the DNA strand 105, consisting of the DNA strands 105-1 and 105-2, which possesses the target sequence 85 and the anchor sequences 83 and 96, is prepared as in example 2 by using the primer 81' that has the same construction with the primer 81 of example 2 except for the target sequence 87.

The DNA strand 105 is denatured to produce the single-strand DNA 105-2, which is hybridized with the primer 32 immobilized to either the subcell 61 of the reaction vessel or the beads placed in the subcells to synthesize the complementary strand 111. Excess of the DNA strand 105-2 is removed by washing. With these procedures, different DNA strands are separately bound to each subcell; in some subcells, no synthesis of complementary strands occurs.

The 3' terminus of the DNA strand elongated by the synthesis of complementary strands possesses a common sequence 96', the strand complementary to the primer 99 containing the same sequence as the anchor sequence 96, at the 3' terminus. A circular strand DNA 112, which has the sequence 96" complementary to the common sequence 96', the substrates for complementary strand synthesis (dNTPs), and enzymes are added to perform the synthesis of complementary strands 114, where the subcells are separated from each other. A large amount of pyrophosphate (nPPi) 115 is thus produced. In this reaction, dATPαS should be used instead of dATP to prevent a direct reaction between luciferin and the substrate for the synthesis.

In specific cases, in which the complementary strand synthesized from the circular DNA 112 does not contain the base species, A, i.e., the DNA sequence 112 except for the sequence 961 does not contain the base species, T, dATP could be removed from the substrates for the synthesis of complementary strands; an expensive reagent, dATPαS is not required in the synthesis, which would lower the costs of the test. This could be an advantage of the method in which not the target sequence but an artificial DNA strand is used as a template. The circular strand DNA as a template is characterized by the fact that it can promote the synthesis of complementary strands endlessly, as long as the substrates for the synthesis of complementary strands are present in a reaction mixture and the DNA polymerase is active. Therefore, an enormous amount of pyrophosphate is produced from a single template DNA.

Figure 14:
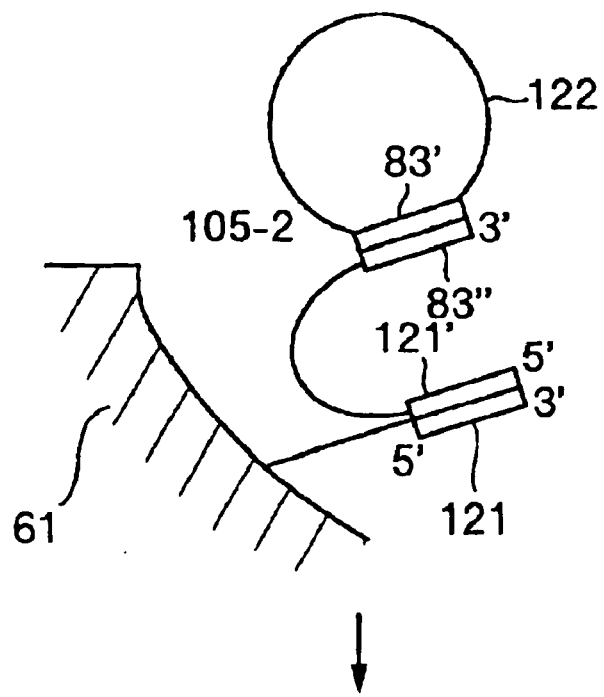
FIG. 14 is a modified example of example 3 of the genetic test of the invention.
Figure 14:
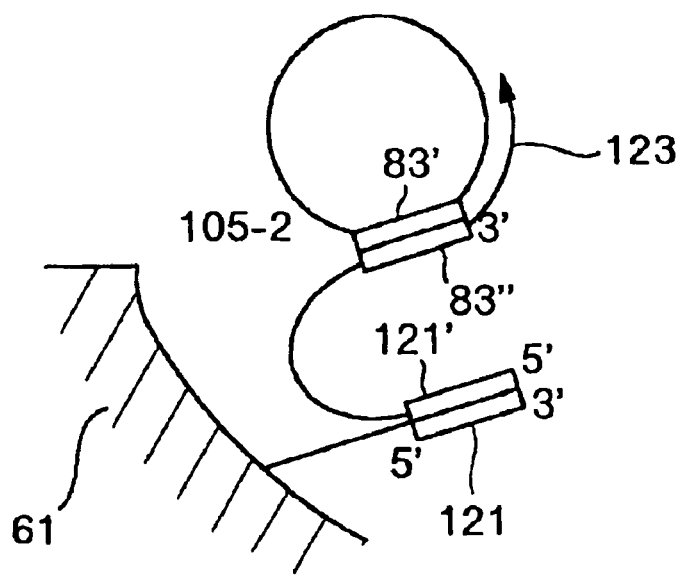

An immobilized and long strand DNA is used in the above example, and FIG. 14 indicates another procedure. The target DNA 105-2 is maintained by the probe 121 immobilized to the subcells and, after removing excess of DNA 105-2, is hybridized with the circular DNA 122 to initiate the synthesis of complementary strands 123. In this case, the probe 121 immobilized to the subcells is used to specifically obtain the target DNA 105-2 that is able to initiate the synthesis of complementary strands 123. The sequence 121' is the sequence of the primer 94, the sequence 83" is complementary to the primer 81', and the sequence 83' is complementary to the sequence 83".

A dendritic DNA could be used instead of a circular DNA for the synthesis of complementary strands to produce a large amount of pyrophosphate. The dendritic DNA is useful for signal amplification, and any sequence could be used without any restriction; both an artificial and a native sequence easily obtained could be available.

EXAMPLE 4

Figure 15:
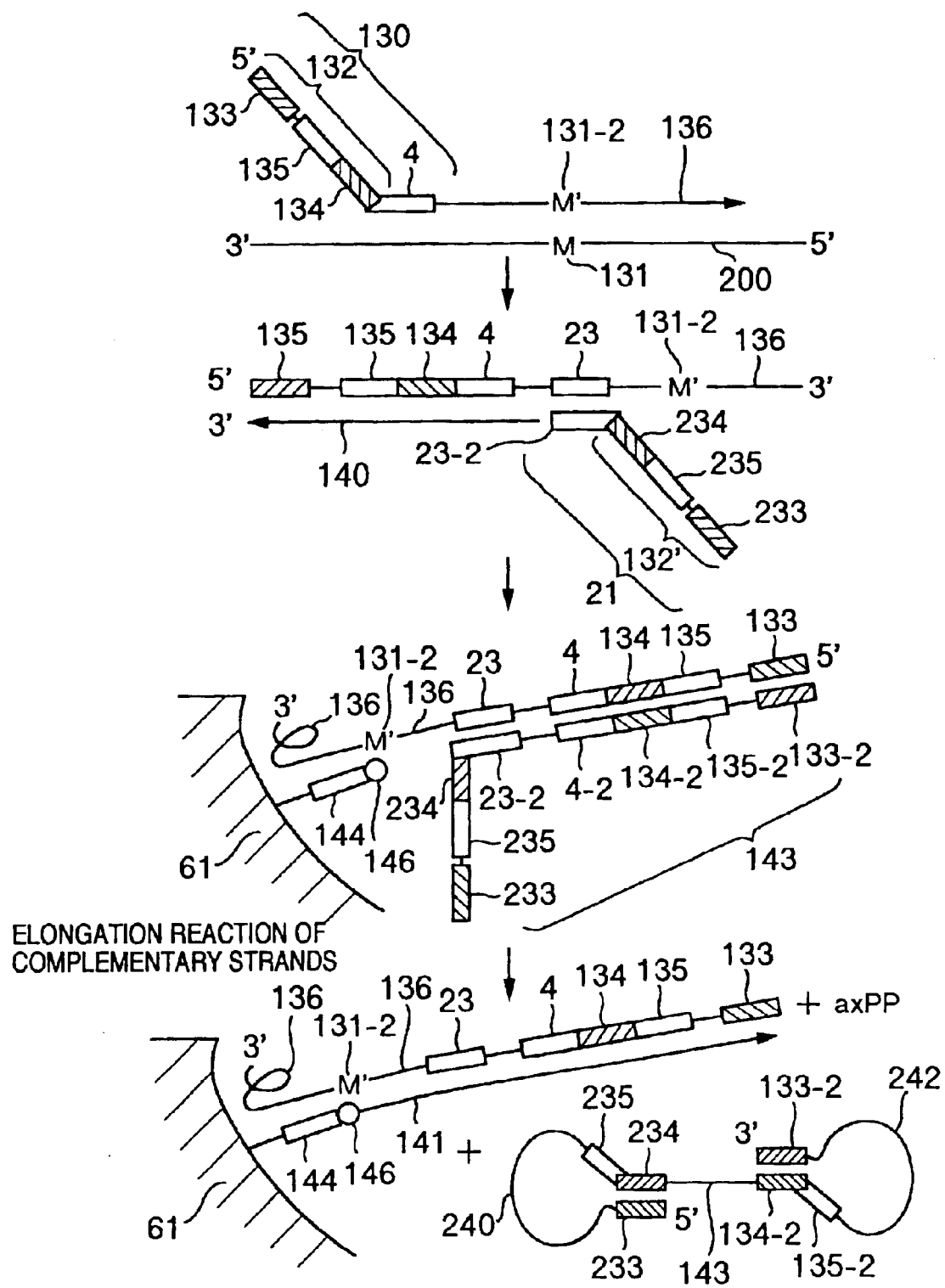
FIG. 15 is production of a large amount of pyrophosphate by self-productive reaction of DNA fragments in example 4 of the genetic test of the invention.

Example 4 is an example, in which a loop-like DNA is prepared and used as a template for synthesis of complementary strands to produce effectively pyrophosphate, the byproduct of complementary strand synthesis. FIG. 15 shows an example of a loop-like DNA that undergoes self-productive reaction to produce a large amount of pyrophosphate in example 4 of the genetic test of the invention.

Although the target DNA 200 could be amplified by PCR, a method for a genetic test without amplification is described here. An anchor primer I (130) is prepared; the primer consists of the anchor region 132 that is not hybridized with the target and the sequence 4 that does hybridize with the target. The anchor region 132 contains the sequence 133 at the 5' terminus, the sequence 134 adjacent to the 5' terminus of the sequence 4, and the sequence 135 adjacent to the 5' terminus of the sequence 134. The sequences 133 and 134 are complementary to each other. M indicates the mutated region 131, and M', the sequence 131-2 complementary to the mutated region 131.

Only a single target is dealt in this example for clear understanding, but multiple targets could be treated in actual experiments. Thus, the description in this example would not interfere the generality.

The synthesis of complementary strands 136 (the synthesis of the first complementary strand) is performed by hybridization of the target DNA 200. The synthesized complementary strand 136 contains the putative mutation-containing region 131-2 at the downstream region (3'-terminal region). After removing excess of the primer I (130), the DNA strands having the synthesized complementary strand 136 are collected. An anchor primer II (21) is hybridized with the 5'-terminal region 23 next to the putative mutated region M' (131-2) in the complementary strand 136 to synthesize the complementary strand 140 (the synthesis of the second complementary strand). The anchor primer II (21) consists of the anchor region 132' that is not hybridized with the complementary strand 136 and the sequence 23-2 that is hybridized with the sequence 23 of the complementary strand 136. The anchor region 132' contains the sequence 233 at the 5' terminus, the sequence 234 adjacent to the 5' terminus of the sequence 23-2, and the sequence 235 adjacent to the 5' terminus of the sequence 234. The sequences 233 and 234 are complementary to each other.

In the complementary syntheses 136 and 140 using the primer I (130) and the primer II (21), respectively, the synthetic reaction could be switched over by the status of mutations by locating the 3' terminus of the primers onto the mutation site 131. However, another method is disclosed in this example; whether the synthesis of complementary strands 141 by the primer III (144) proceeds or not could regulate the production of a large amount of pyrophosphate.

By the synthesis of complementary strands using the primer II (the anchor primer 21), the complementary strand 140 is synthesized, and the double-strand DNA is produced.

However, the anchor region 132' remains as a single strand, as well as the sequence 131-2 that is subjected to examination of mutation. After removing excess of the anchor primer 21, the DNA strand containing the synthesized complementary strand 140 is added to the reaction vessel. The primer III (144) immobilized to the subcell 61 (if the primer III (144) is not immobilized to the subcell 61, moving of the DNA-containing solution should be prevented among the subcells) is designed to be hybridized with the single strand region of the complementary strand 136, a constituent of the double-strand DNA, so that the 3'-terminal region 146 matches with the site subjected to examination of mutation.

Different species of the primer III are immobilized separately to each subcell of the reaction vessel to capture the target double-strand DNA. After the capture, excess of the DNA-containing solution is removed, and the subcells are separated from each other by partitioning plates. The DNA polymerase, the primer IV (250, not shown), the substrates for complementary strand synthesis and the chemiluminescent reagents are added to each subcell of the reaction vessel, where the synthesis of complementary strands and the subsequent chemiluminescent reaction are performed separately. With the use of separated subcells, multiple mutations can be detected simultaneously. The method could be applied for examination of a single mutation, and the primer III (144) is not necessarily immobilized in this case.

When the 3' terminus 146 of the primer III (144), which captures the double-strand DNA, matches with the test site M' (131-2) of the target complementary strand 136, the synthesis of the complementary strand 141 (the synthesis of the third complementary strand) is allowed to proceed by using the complementary strand 136 as a template. A large amount of pyrophosphate (a×PPi) is produced, and the DNA strand 143 that has formed the double-strand DNA is released from the DNA strand containing the complementary strand 136. The 5'-terminal sequence 233 of the DNA strand 143 can be self-hybridized with the sequence 234, and the 3'-terminal sequence 133-2 can be self-hybridized with the sequence 134-2, which form a loop structure 240 and 241, respectively.

Using the DNA strand 143 as a starting substance, self-hybridization and complementary strand synthesis are repeated to produce a large amount of pyrophosphate, as indicated in LAMP method for replication of DNA strands (Ref. 9: Nucl. Acids Res.: 28, e63 (2000)). Although replication of DNA strands is aimed at in LAMP method, the purpose of this invention is detection of SNP mutations and production of a large amount of pyrophosphate. Therefore, any template DNA such as an artificial sequence without target sequences could be used for repetitive synthesis of complementary strands. In anchor primer I (130) and anchor primer II (21), introduction of two sets of the complementary sequences that are self-hybridized, 133 and 134, and, 234 and 233, makes it possible to produce a large amount of pyrophosphate with the aid of an arbitrary primer that does not contain the target sequence.

Furthermore, resynthesis of complementary strands could be conducted by degrading the synthesized DNA strands by exonucleases. Detection of pyrophosphate is as described in examples 1, 2 and 3. In normal LAMP method, in which DNA strands are amplified using a loop sequence, sequences specific to targets are selected for the primer IV (250) that is hybridized with a loop formed by self-hybridization of the DNA strand 143. When analyzing a large number of target species, the same number of primers should be prepared, which would be a big labor. To solve this, a loop region could be constructed by artificial sequences that are not identical to the target sequences, and the primer IV (250) could be used as a common primer, which is hybridized with the loop region formed by self-hybridization of the DNA strand 143. In this case, it is the primer III (144) immobilized to each subcell that selects the target and triggers the synthesis of complementary strands.

Figures 16, 17:
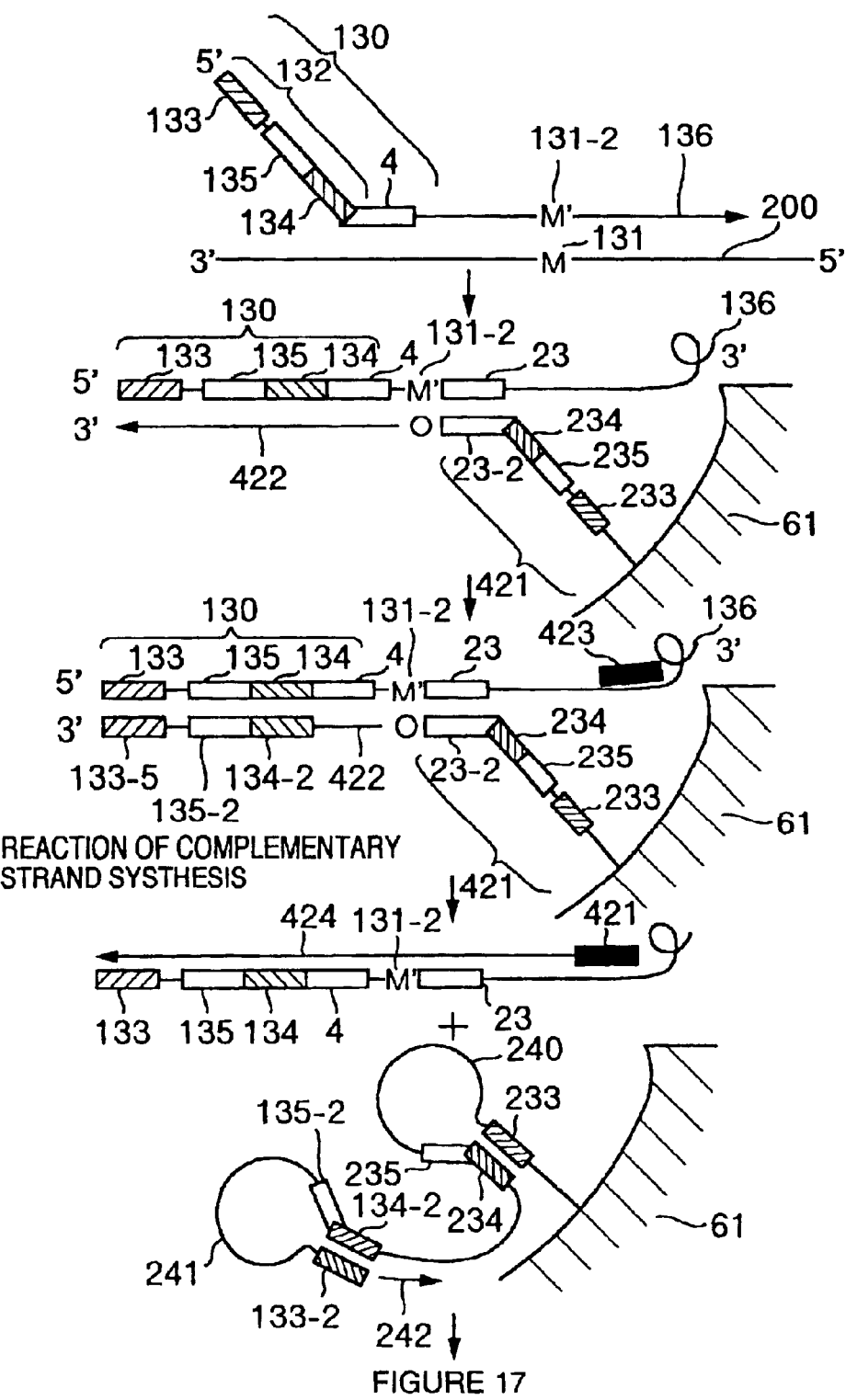
FIG. 16 is an example in which a part of the self-productive reaction of the DNA fragments is performed on the surface of the reaction vessel in example 4 of the genetic test of the invention.
FIG. 17 is an example in which a part of the self-productive reaction of the DNA fragments is performed on the surface of the reaction vessel in example 4 of the genetic test of the invention (following FIG. 16).
Figure 17:
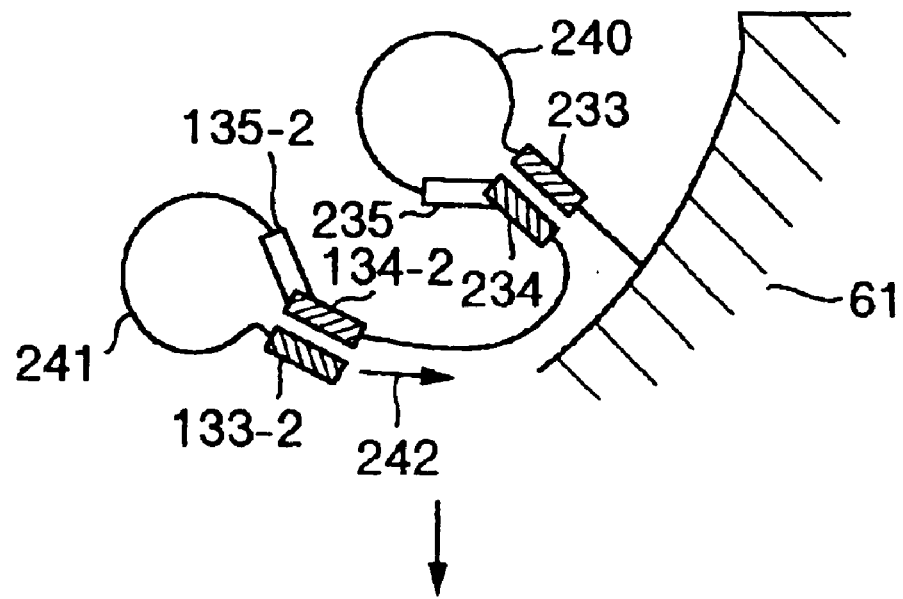
Figure 17:
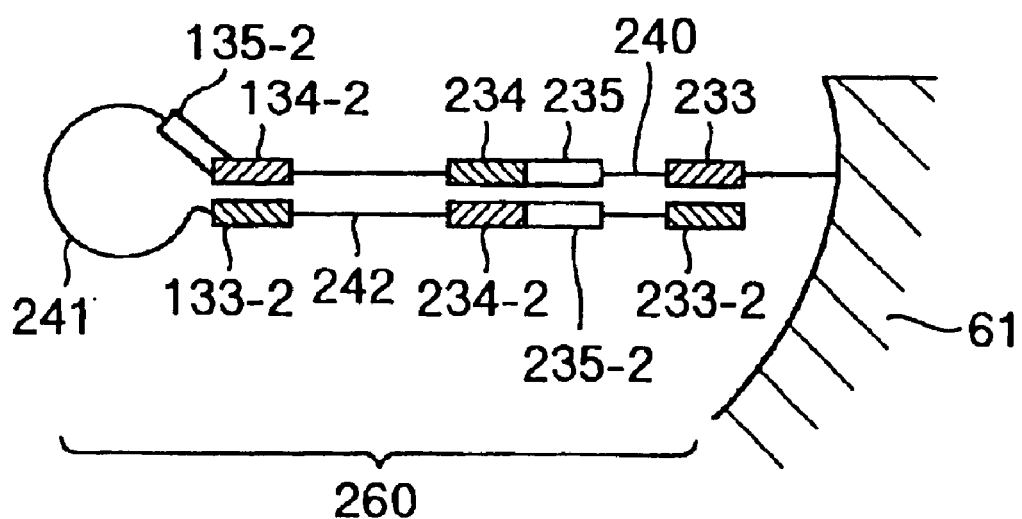

In example 4, the reaction product of the complementary strand synthesis containing the double-strand DNA 143 is added to the reaction vessel after the second synthesis of complementary strands, followed by the third and the later synthesis of complementary strands and the chemiluminescent reaction. As another method, the second and the later reactions could all be performed in the reaction vessel or the subcells as shown in FIGS. 16 and 17. Shortly, the DNA strands including the complementary strand 136 are added to the reaction vessel and hybridized with the probe II (primer II) 421 immobilized to the subcell 61. Different species of the probe II are separately added to each subcell, where the synthesis of complementary strands is allowed to occur for each of the different targets.

For this step, the 3' terminus of the probe II (421) is carefully designed to be hybridized with the M' site of the DNA strand 136 subjected to examination of mutations. If there is an expected mutation complementary to the probe, the extension 422 of the probe II is initiated. However, when the target does not contain any complementary sequence or expected mutation (depending on the situation, it could be reversed), the elongation of complementary strands does not occur. If the elongation is initiated, double strands are partially formed. The primer III (423) is hybridized with a single strand at the 3'-terminal region of the DNA strand containing the complementary strand 136 to perform the synthesis of complementary strands 424. The primer III (423) is therefore added to the reaction vessel 61 after the synthesis of complementary strands using the primer II (421). When the elongation reaction 242 occurs, a hairpin-like DNA 260 that contains a loop structure 241 immobilized to the reaction vessel is produced.

The primer III (423) is used for making single strands from double strands. Instead of using this primer, the subcells could be heated to generate single strands. By heating and cooling the reaction system, the complementary strand (the complementary strand by the elongation reaction of the primer II (421)) that is self-hybridized is elongated to form a hairpin-like structure possessing the loops 240 and 241; the primer III is not required in this case. The reactions following the hybridization of the primer IV (250) with the loop region 241 and the repetitive synthesis of complementary strands are the same as in LAMP method.

After performing the complementary strand synthesis with the primer II immobilized to beads and subcells, loop-like single strands could be formed by increasing the temperature to 95–100° C. and then decreasing to approximately 40° C., which allows repetitive synthesis of complementary strands. If the sequences of the terminal loops 240 and 241 are made to be rich in A and T, it is possible that the slight increase in temperature induces the complementary strand synthesis repeatedly. Otherwise, by using the primers that can hybridize with loop structures, single strands could be prepared to form a loop sequence, which is followed by the synthesis of complementary strands.

In this case, the anchor sequence of the primer I should be designed so that the loop region is common to various DNA fragments. Addition of the primer III that is hybridized with the anchor sequence of the primer I initiates the synthesis of complementary strands, and the DNA partially containing double-strand region is produced. The single-strand region possesses the 3' terminus, and forms a loop by self-hybridization, which induces the synthesis of complementary strands again. By repeating these steps, more pyrophosphate could be produced.

EXAMPLE 5

Figure 18:
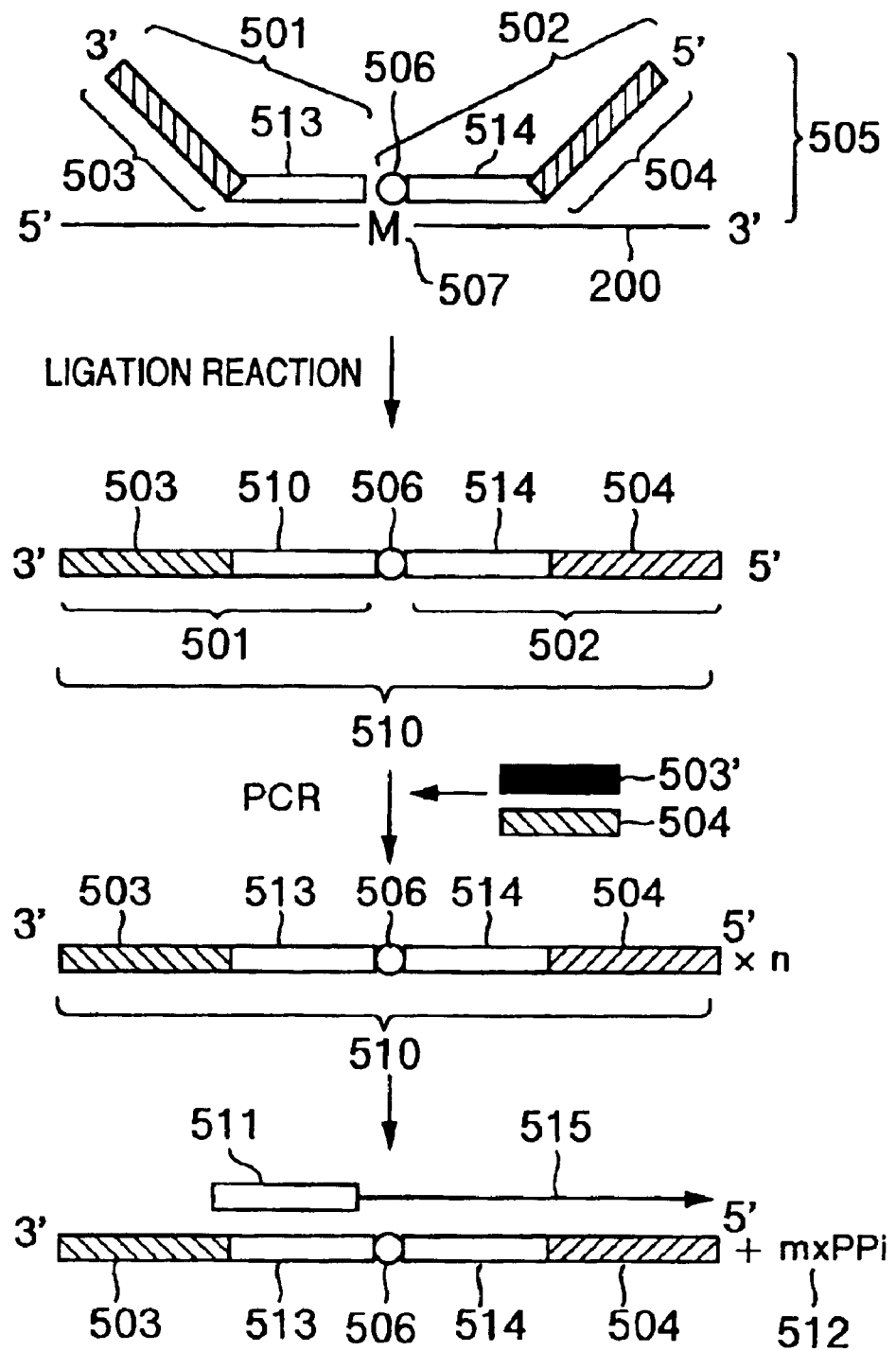
FIG. 18 is an example in which ligation reaction of the anchor probes of the two primers is utilized in example 5 of the genetic test of the invention.

Example 5 is a method, in which detection of targets and identification of mutated bases are achieved by a ligation reaction. FIG. 18 shows an example, in which the ligation reaction of anchor probes of two primers are used in example 5 of the genetic test of the invention. Two anchor probes 501 and 502 that are hybridized with sequence regions of the genes subjected to examination are prepared for each target.

Anchor regions 503 and 504 are the universal sequences, which are connected to the 3' and 5' terminus, respectively. The anchor probes 501 and 502 are constructed so that the 3' terminus 506 opposite to the anchor region 504 and the 5' terminus opposite to the anchor region 503 are connected to make a single DNA fragment. As shown in 505, the sequences 513, 514 and 506 are hybridized with the target in tandem. Either the 3' terminus of the anchor probe 502 or the 5' terminus of the anchor probe 501, which is involved in ligation reaction, should be located exactly on the mutation site M (507).

FIG. 18 is an example, in which the 3' terminus 506 of the anchor probe 502 corresponds to the mutation site M (507) in the target. If the terminal sequence is not completely complementary to the target sequence, the ligation reaction does not occur. This means that the presence or absence of mutations could be determined by whether the ligation reaction occurs or not. After the ligation reaction, excess of the probes 501 and 502 is washed away, and double strands are denatured to single strands to obtain the DNA fragment 510 produced in the ligation reaction.

The fragment 510 is PCR-amplified by using the primer containing the sequence 503' complementary to the universal sequence 503 and the primer containing the universal sequence 504. The amplified product is collected as single strands by asymmetry PCR or the step for producing single strands using biotin-avidin binding. The obtained strands are added to the reaction vessel and hybridized with the probe 511 in the subcells to initiate the synthesis of the complementary strand 515. Pyrophosphate produced during the synthesis is used for developing chemiluminescence. The presence of the product can be detected by a photosensor, which consequently indicates the presence of target genes and mutations.

Figure 19:
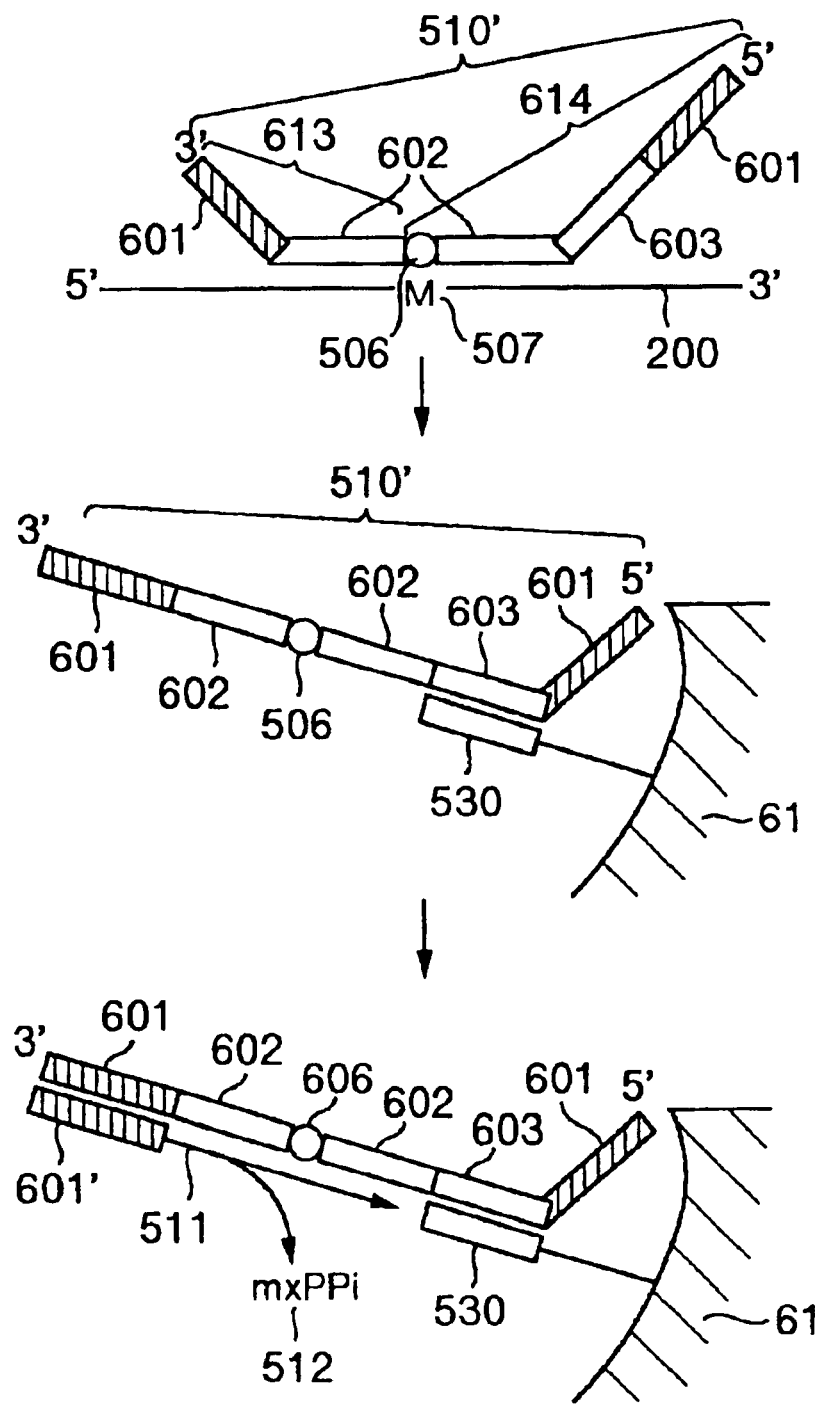
FIG. 19 is a modified example in which reaction on the solid phase is used in example 5 of the genetic test of the invention.

As shown in FIG. 19, the recognition sequence 603 could be introduced between the anchor sequence 601 and the sequence 602 that is hybridized with the target. By this means, the single-strand DNA fragment 510' is prepared as indicated in FIG. 18, and captured by the subcell 61 utilizing the recognition sequence 603 as a marker. The probe 530 maintained in the subcells consists of the multiple probes containing various recognition sequences without any relation to the target sequences, each of which is separately immobilized to each subcell. The sequence 603, complementary to the probe 530 that is immobilized to the subcells and has a recognition sequence for collecting targets, could be introduced to the probe 614, which makes it possible that the reaction cells immobilizing probes are used universally.

The recognition sequence 603 for collecting the PCR product is introduced to one of the primers that are hybridized with the target. Detection of chemiluminescence described below is the same as the examples shown above. Pyrophosphate 512 produced during the elongation reaction 511 is detected by luciferin and luciferase. In this case, the presence of mutations has been already judged during the ligation, and the primer 601' for the synthesis of complementary strands could be simply added to each subcell, where the synthesis of complementary strands is performed. Otherwise, the probes for collecting the targets or universal primers could be used as a primer for complementary strand synthesis. A variety of detection method could be applied to these cases. Details are omitted to avoid redundancy.

EXAMPLE 6

Figure 20:
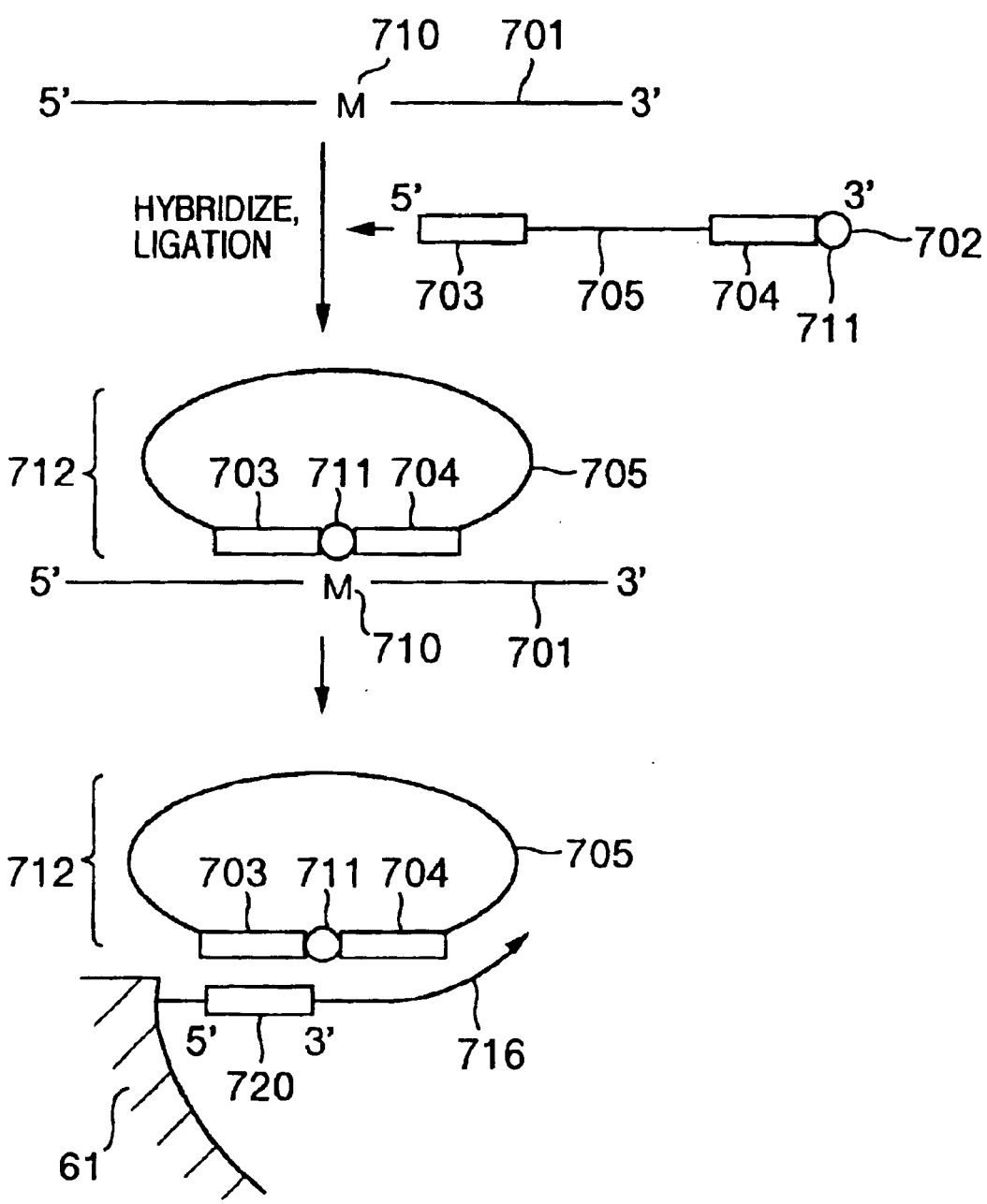
FIG. 20 is an example in which the probe DNA for detecting SNPs that becomes circular by ligation reaction is used in example 6 of the genetic test of the invention.

Example 6 is the example, in which the probe 702 whose both termini are hybridized with the target 701 in tandem. FIG. 20 demonstrates an example, in which the probe DNA that could form a ring in ligation reaction is used for detecting SNPs in example 6 of the genetic test of the invention. The probe 702 consists of the sequences 703 and 704 (equivalent to probes I and II) at the both termini, which are hybridized with the targets, and the universal sequence I (705) in the middle region.

The probe 702 is hybridized with the target 701 to perform the ligation reaction. Either terminus 711 of the probe 702 should be adjusted to be located at the mutation site 710. When the terminus is complementary to the target, the ligation reaction is initiated to form the circular DNA 712 from the DNA strand. On the other hand, when the terminus is not complementary to the target, the DNA strand remains as a linear form. After the ligation reaction, unreacted probe 702 is removed by washing.

The circular DNA 712 added to the reaction vessel is hybridized with and captured by the partial sequence 720 of the DNA probe (probe III) immobilized to the subcells. The partial sequence 720 of the DNA probe for capturing (probe III) is complementary to the 5'-terminal sequence of the probe 702 that is hybridized with the target, and is hybridized with the sequence 703, which promotes the complementary strand synthesis to produce the complementary strand 716 to the sequence 704. This construction is designed to prevent the synthesis of complementary strands when the probe 702 does not form a circular structure. Each species of the probe 720 is immobilized to the subcell or is stored with matrix in the subcells in according to their sequences.

Figures 21, 22:
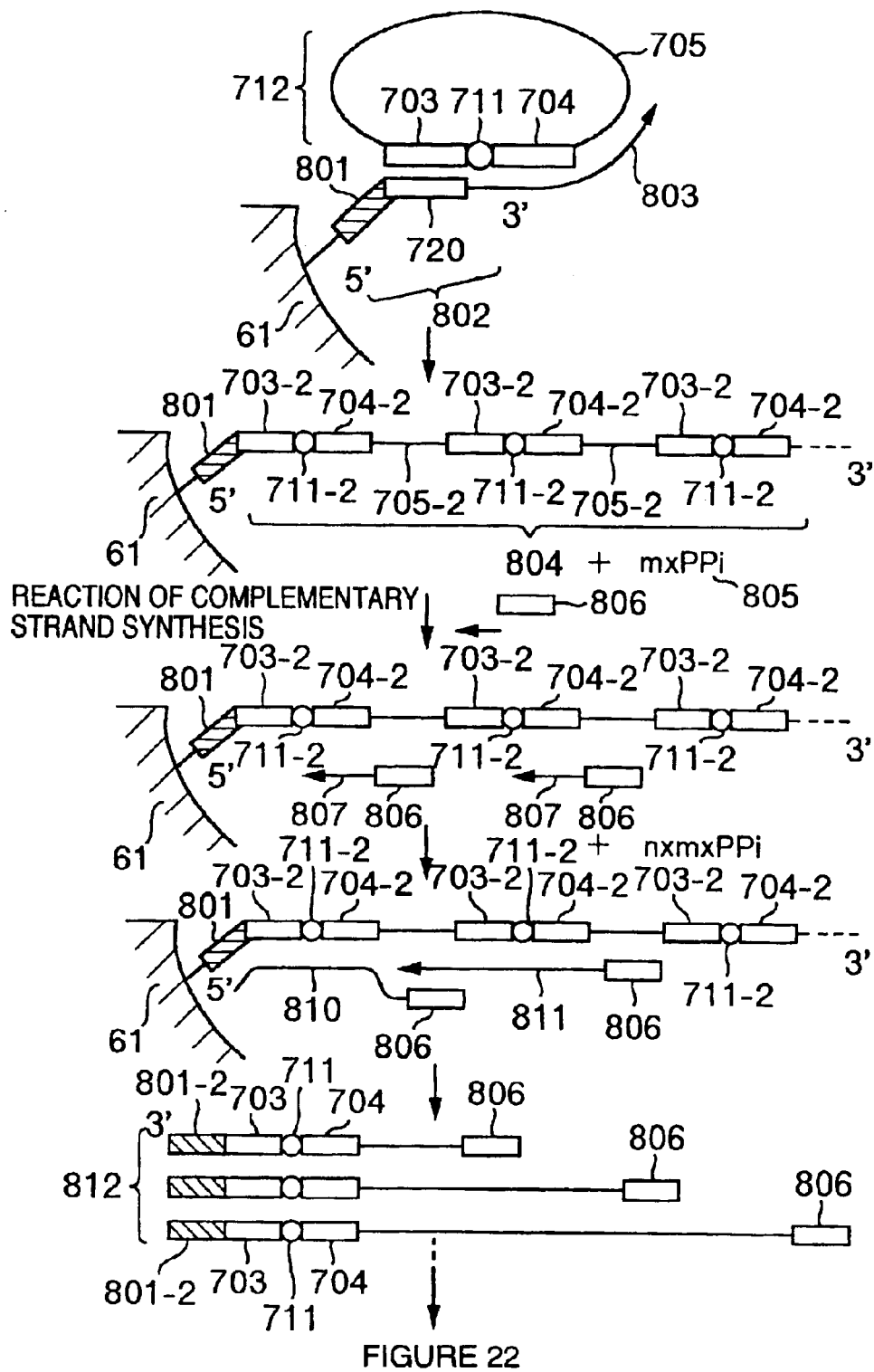
FIG. 21 is another example in which the probe DNA for detecting SNPs that becomes circular by ligation reaction is used in example 6 of the genetic test of the invention.
FIG. 22 is another example in which the probe DNA for detecting SNPs that becomes circular by ligation reaction is used in example 6 of the genetic test of the invention (following FIG. 21).
Figure 22:
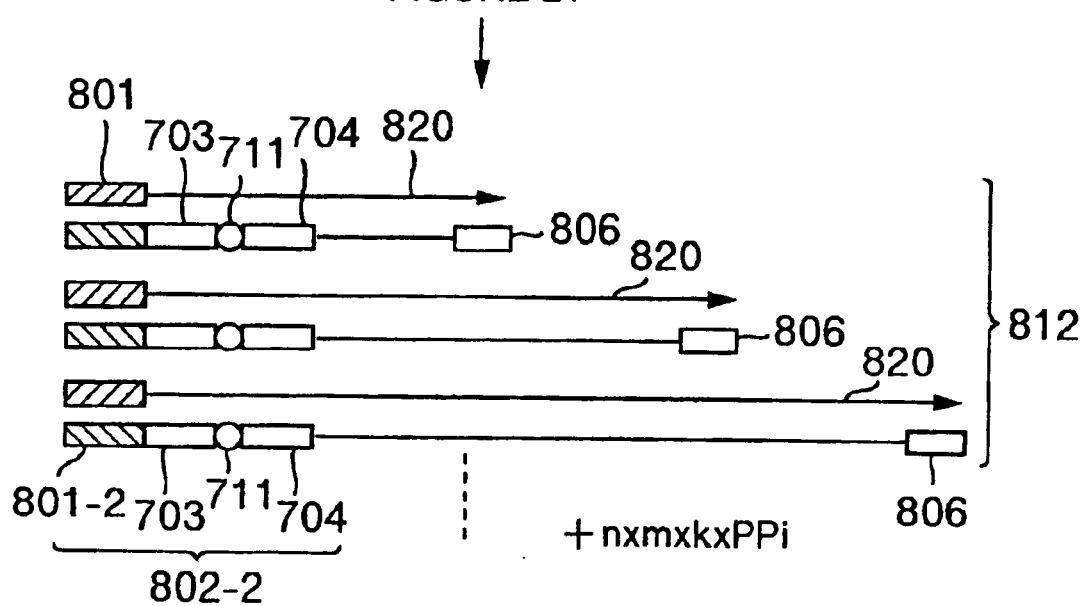

In addition to the sequence 720 that is hybridized with the circular DNA 712, the universal sequence II (801) could be introduced to the 5' terminus of the probe III for signal amplification as described below (FIGS. 21 and 22). FIG. 21 shows another example, in which the DNA probe that becomes circular by the ligation reaction is used for detecting SNPs. FIG. 22 follows FIG. 21.

The probe III (802) hybridized to the circular DNA promotes the repetitive synthesis of the first complementary strand 804, which is not circular but contains the chain repetitive sequence, by using the circular DNA 712 as a template during the synthesis of the complementary strand 803. During this synthesis, a large amount of pyrophosphate (805) is produced. To amplify the signal, the primer IV (806) having the partial sequence of the universal sequence I (705) could be introduced to the reaction. By this means, the primer IV (806) is hybridized with a part of the sequence 705-2 complementary to the repetitive universal sequence I (705) present in the synthesized complementary strand 804, and produces the second complementary strand 807 one after the other.

The complementary strand 804' contains multiple 705-2 regions that are complementary to the universal sequence 705, and the primer IV (806) is hybridized with the sequences 705-2 one after the other to promote the synthesis of complementary strands. The synthesis of the second complementary strand 807 is initiated near the 5' terminus of the complementary strand 804. During this synthesis of the complementary strand 807, the synthesis of complementary strands 811 proceeds with unsticking the strand 807 from the 3' terminus as shown in 810. As a result, many species of the third complementary strand 812, with various length corresponding the circle length, are prepared.

The complementary strand 812 consists of a set of the DNA that contains the sequence 802-2 complementary to the sequence of the probe III (802) at the 3' terminus. Therefore, the complementary strand 812 possesses the sequence 801-2 complementary to the universal sequence 801 near the 3' terminus. When the primer V (801) containing the universal sequence II (801) is added, the synthesis of complementary strands undergoes using the third complementary strand 812 as a template, and the forth complementary strand 820 is produced.

With these procedures, a large amount of pyrophosphate is produced. All the reactions should be done at the constant temperature, 50–60° C., to inhibit the heat degradation of dNTP during the course of the complementary strand synthesis. The degradation should be inhibited as much as possible, because the degradation of dNTP produces pyrophosphate, which develops the background luminescence interfering the photodetection.

Instead of dATP that could react with luciferin, other substrates such as dATPαS with no or less reactivity should be used. Then pyrophosphate is converted to ATP and reacted with luciferin to obtain chemiluminescence. Various methods are available for chemiluminescent detection as described previously.

To achieve much higher detection sensitivity, the circular DNA containing the universal sequence II (801) could be substituted for the primer V (801); a set of the second complementary strands is hybridized with the circular DNA, which elongates the complementary strands and prepares a large group of complementary strands.

EXAMPLE 7

Figure 23:
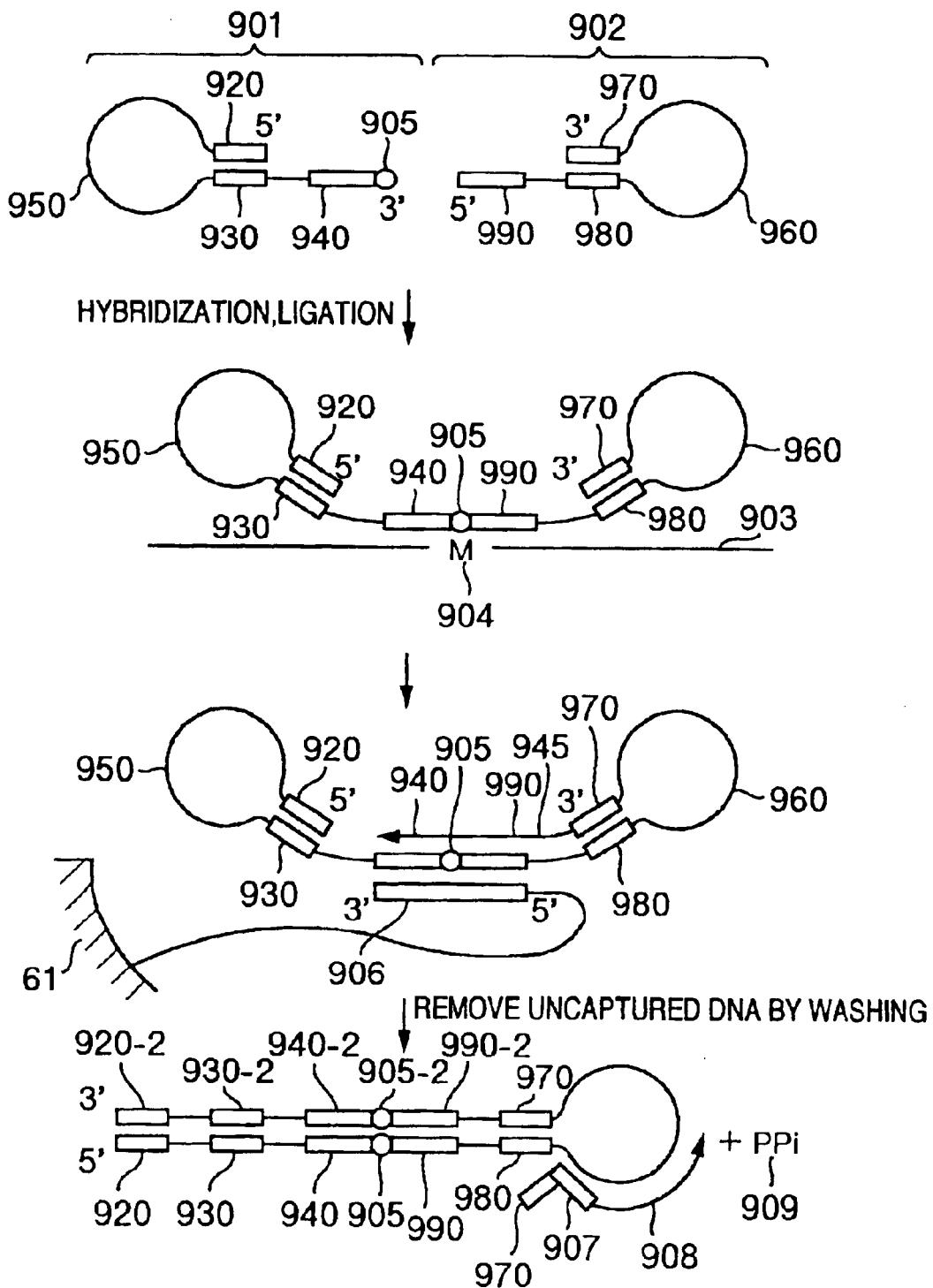
FIG. 23 is an example in which the self-productive probes are used in the reaction involving the ligation reaction in example 7 of the genetic test of the invention.

In example 7, two probes, 901 and 902, are used. The probe 901 contains the loop-like sequence 950 at the 5' terminus, the sequence 930 that is hybridized with the 5' terminal sequence 920 and the sequence 940 that is hybridized with the target 903 and is connected to the 3' terminal. The probe 902 consists of the loop-like sequence 960 at the 3' terminus, the sequence 980 that is hybridized with the 3' terminal sequence 970 and the 5' terminal sequence 990 that is hybridized with the target 903. In example 7, the two primers 901 and 902 that contain a loop structure at the 3' and 5' termini, respectively, are conjugated by the ligation reaction, and the third primer is used for repetitive synthesis of complementary strands, which produces a large amount of pyrophosphate in subcells. FIG. 23 illustrates an example, in which self-productive probes are used in the reactions involving the ligation in example 7 of the genetic test of the invention.

The anchor probes 901 and 902 that are self-hybridized are prepared for each target 903 species as shown in FIG. 23. The anchor probes 901 and 902 are hybridized with the target 903 to perform the ligation reaction. On this occasion, the 3' terminus 905 of the probe 901 and the putative mutation site M (904) should be located in accordance with each other. If the mutation site is not complementary to the 3' terminus of the probe 901, the ligation does not occur.

The ligated DNA strands are left with the target, and excess of the primers 901 and 902 is removed by washing. The ligation product of single strand is added to the reaction vessel and captured by the specific probes 906 immobilized to the subcell 61 via its 5' terminus. Excess of the DNA, or the single-strand ligation product, is washed away. When the sequence consisting of the sequences 940, 905 and 990 is complementary to the specific probe 906, the ligation product is captured by the specific probe 906, which is followed by the synthesis of complementary strands 945.

The anchor primer possessing the sequence 907 that is hybridized with the single-strand region of the loop and is connected to the 5' terminal sequence 970 (anchor region), the substrates for complementary strand synthesis (dNTP, in which dATP is replaced by dATPαS) and the DNA polymerase are mixed. The elongation of complementary strands 908 proceeds, and a large amount of pyrophosphate 909 is obtained. Using this pyrophosphate, chemiluminescent reaction is performed for photodetection. These processes have been described in detail previously. The sequences 920-2, 930-2, 940-2, 905-2 and 990-2 are complementary to the sequences 920, 930, 940, 905 and 990, respectively.

Figure 24:
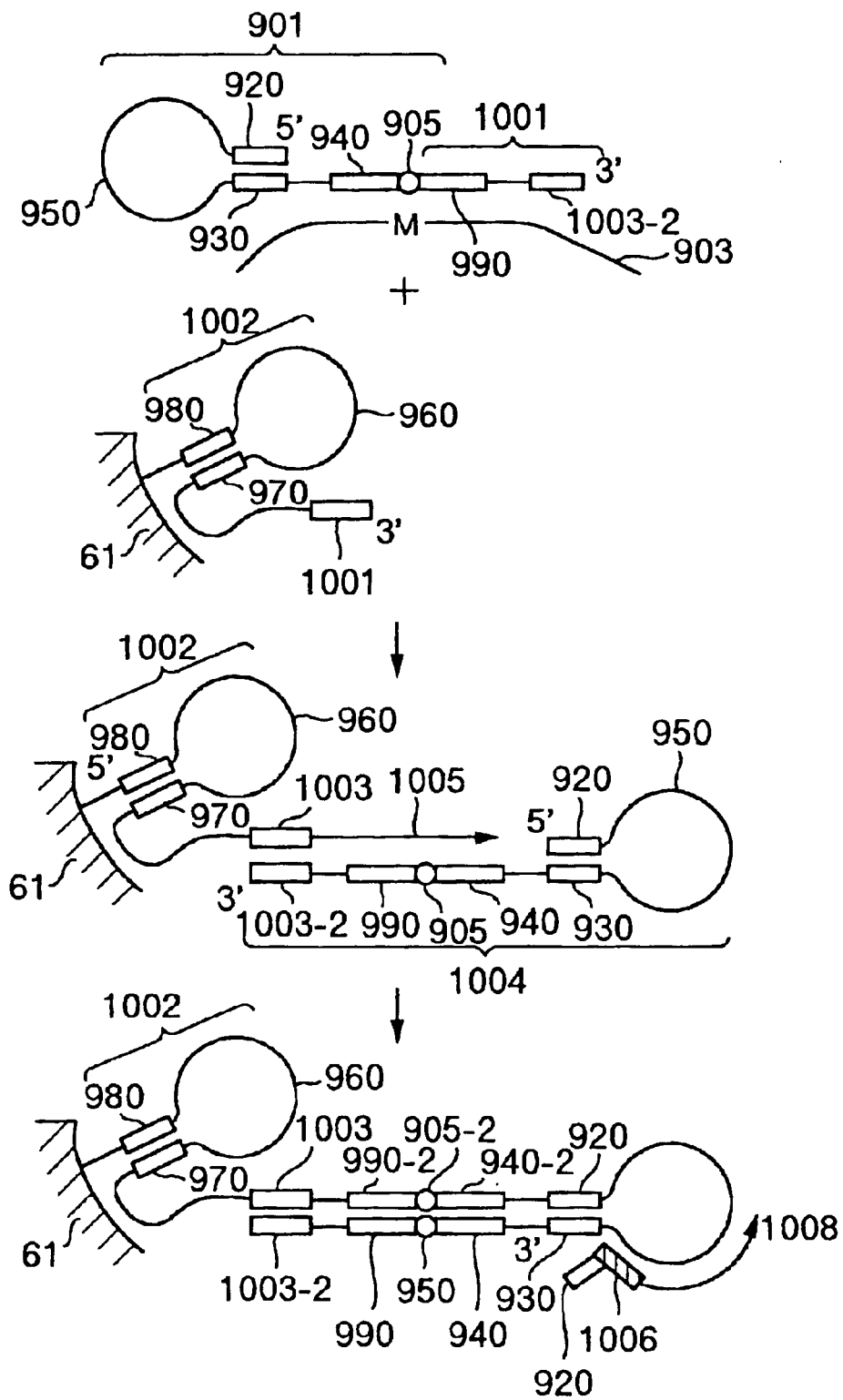
FIG. 24 is an example in which the self-productive reaction of the DNA fragments proceeds on the surface of the reaction vessel in the ligation reaction used in example 7 of the genetic test of the invention.

In example 7, the two probes 901 and 902 that are to be ligated contain a loop sequence at the 3' and 5' terminus, respectively. The probe 1001 does not possess any loop structure. Only the probe 901 that has a single loop at the 5' terminus could be used. FIG. 24 shows an example, in which ligation reactions are used in example 7 of the genetic test of the invention, and demonstrates that the self-productive reaction of DNA strands occurs on the surface of the reaction vessel. In example 7, the probes 901 and 1001 are hybridized with the target 903, and the DNA produced by ligation is not used for further synthesis of complementary strands.

The probe 1002 that contains the sequence 1003 that is hybridized with 3'-terminal sequence 1003-2 of the probe 1001 at the 3' terminus is prepared in the subcells. The probe 1002 is immobilized to the solid surface 61 via the 5' terminus of the sequence 980 that is hybridized with the sequence 970. The probe also contains the loop sequence 960 at the 5' terminus and the sequence 1003 at the 3' terminus, which is hybridized with the 3'-terminal sequence 1003-2 of the single-strand ligation product 1004. After hybridizing the probe 1002 with the ligation product 1004, the synthesis of complementary strands 1005 is carried out.

Excess of the DNA (the ligation product 1004) is removed, and the DNA that has been hybridized with the probe 1002 is isolated by increasing the temperature. Then the reagents for complementary strand synthesis and the primer containing the sequence 1006 that is hybridized with the loop structure and the anchor sequence 920 are added, as well as the chemiluminescent reagents for pyrophosphate finally produced. The synthesis of complementary strands is initiated after the subcells are separated from each other. The primer sequence 1006 is hybridized with the loop region 950, which induces the synthesis of complementary strands 1008. A large amount of pyrophosphate PPi is thus produced.

The 3' terminus of the DNA strands produced by the complementary strand synthesis using the primer sequence 1006 is single strand. This region is self-hybridized as in example 4 and promotes the synthesis of complementary strands again. By repeating this reaction, an enormous amount of pyrophosphate is produced. Pyrophosphate is converted to ATP, which undergoes the chemiluminescent reaction in the presence of chemiluminescent reagents such as luciferin and enzymes. The chemiluminescence is detected by a photosensor, which clarifies the presence of mutations or target genes in a sample.

EXAMPLE 8

Figure 25:
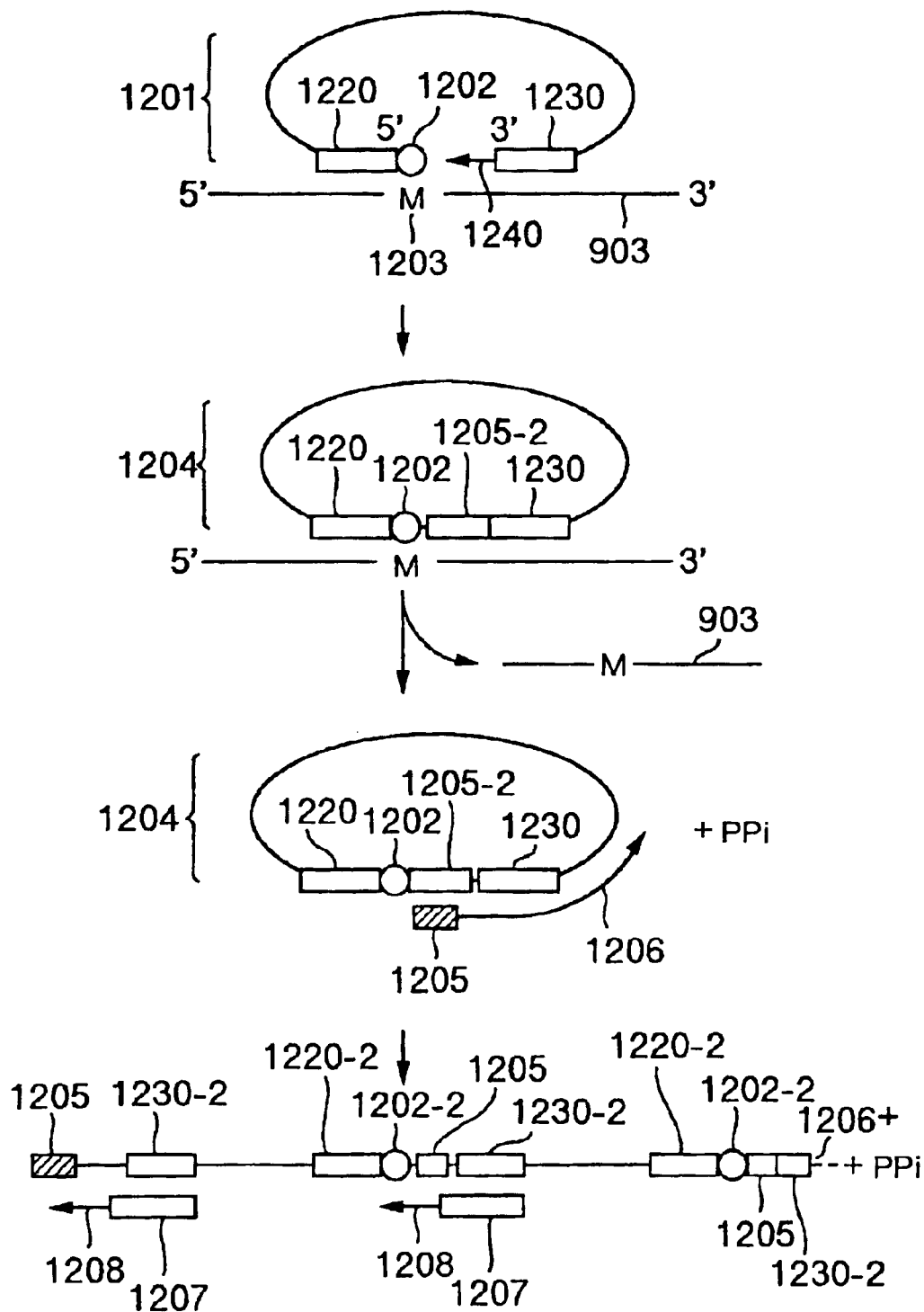
FIG. 25 is an example in which repetitive sequences are obtained by the reaction of elongation of complementary strands and the ligation reaction in example 8 of the genetic test of the invention.

Example 8 is an example, in which the probe 1201 that is hybridized with the target is detected as a circular DNA by ligation after synthesis of complementary strands. FIG. 25 shows an example, in which repetitive sequences are obtained by the elongation reaction of complementary strands and the ligation reaction in example 8 of the genetic test of the invention. The sequence of the synthesized complementary strand is a new sequence that has not been in the probe. Using this sequence as a recognition sequence, each target, i.e., the circular DNA formed by complementary strand synthesis and ligation, is discriminated, and the synthesis of complementary strands is performed in each subcell, which is followed by detection of pyrophosphate. Compared to a simple ligation, DNA sites subjected to examination can be more specifically selected.

The probe 1201 consists of the sequence 1220 that is hybridized with the target 903, the 5'-terminal sequence 1202 connected to the 5' terminus of the sequence 1220, and the sequence 1230 whose 3' terminus is hybridized with the target 903.

Although the reaction step requires an extra synthesis of complementary strands in addition to the ligation, this would not be a big problem because the entire targets corresponding to all of the test sites could be processed as a single mixture. Mutation sites could be recognized by agreement or disagreement of the 3' terminus of the probe 1201 (the complementarity of the 3' terminus of the primer and the target), or by the occurrence of the ligation by locating the 5' terminus 1202 of the ligated probe 1201 on the mutation site M (1203).

Mutations may not be recognized during the preparation of circular DNA. Instead, the 3' terminus of the primer used in the complementary synthesis of circular strands is allowed to be located on the mutation site, and the synthesis of complementary strands could be regulated by agreement or disagreement of the 3' terminus of this primer (the complementarity of the 3' terminus of the primer and the target), which could judge the presence of mutations. After the synthesis of complementary strands 1240, the circular DNA 1204 is prepared by ligation. Excess of the probe 1201 is removed by washing while the ligation product is hybridized to the target (in most cases, genomic DNA).

Although excess of the DNA probe 1201 is removed, the circular DNA 1204 is maintained with being hybridized with the target 903. After washing, the circular DNA 1204 is released from the target 903 and used as a test subject. The circular DNA thus obtained contains the sequence that has not been present in the original probe 1201, i.e., the sequence that is elongated by the synthesis of complementary strands. Then different species of the probe 1205 are separately added into each subcell by using the elongated sequence 1205-2 as a marker. After selecting specific circular DNA, the synthesis of complementary strands 1206 is performed in the subcells. Probe 1205 is complementary to sequence 1205-2. The probe 1201 left in the reaction mixture does not interfere the synthesis because a newly synthesized sequence is recognized by the probe 1205.

The primers complementary to the complementary strand 1206 to be synthesized and the circular DNA possessing the sequence complementary to the DNA strands that is formed by elongation of this primer are added to the reaction. When the probe 1205 is hybridized with the circular DNA 1206 to induce the synthesis of complementary strands 1206, the probe 1207 is hybridized with the complementary strand 1206 to produce the complementary strand 1208. The synthesis of complementary strands is initiated at a number of sites in association with the elongation of the complementary strand 1206. The complementary strand previously synthesized is released as a single strand by the next synthesis of complementary strands, which accelerates the synthesis of the complementary strand 1208. The complementary strand 1208 is hybridized with the previously added circular DNA and initiates the synthesis of circular complementary strands. The sequences 1220-2, 1202-2, and 1230-2 are complementary to the sequences 1220, 1202 and the 1230.

Synthesis of complementary strands occurs as a cascade reaction in this way, which consequently produces an enormous amount of pyrophosphate PPi. Pyrophosphate is converted to ATP and then reacted with luciferin in the presence of luciferase, which develops chemiluminescence. As the substrates for complementary strand synthesis, dNTP analogs that are not reacted with luciferin are recommended; e.g., dATPαS could be substituted for dATP. It is also recommended that poly T chains are prepared in complementary strand synthesis by using an artificial DNA sequence constructed extensively by poly A sequences, so that the substrate bases with high reactivity against luciferin are excluded from the reaction.

Characteristics of the method for the DNA test of the invention are described.

1. This method is the method for a DNA test and a genetic test, which is characterized by the following steps:
   (1) A step, in which a group of primers consisting of multiple primer species is added to a sample subjected to examination, and simultaneous synthesis of complementary strands is performed.
   (2) A step, in which the DNA probes are designed so that the elongation of complementary strands of the probes is affected by the presence or absence of base mutations in the DNA subjected to examination. A group of probes consisting of at least the same number of such probes as that of the target species is used for the elongation of complementary strands.
   (3) A step, in which the reaction of complementary strand synthesis using a variety of targets or the sequences complementary to the targets as a template and the following reaction, in which pyrophosphate resulting from the complementary strand synthesis is converted to ATP and reacted with chemiluminescent substrates to develop luminescence, are performed in the subcells compartmentalized for each target. Mutations present in genes or DNA are detected by monitoring the luminescence thus obtained.

2. In the method according to 1, the method is characterized by the following steps:
   (1) A step, in which a group of the first primers that are hybridized with the subject DNA samples to induce the complementary strand synthesis consists of the anchor primers having an arbitrary sequence at the 5' terminus, each of which is hybridized with each of the entire DNA subjected to examination.
   (2) A step, in which, after removing excess of the primers, the synthesis of complementary strands is performed by using the second anchor primers having the sequence complementary to the first complementary strands thus synthesized. In this synthesis, the DNA fragments for a test having either the first or the second anchor sequence at least at one terminus are prepared.

(3) A step, in which the number of copies of these DNA fragments is amplified by using at least one of the terminal anchor sequences as a priming region.

3. In the method according to 1 or 2, the method is characterized by the following steps:
   (1) A step, in which single strands prepared from the amplified DNA strands are used as a template for synthesis of complementary strands. The primer is hybridized with the target, so that the 3' terminus of the primers is located exactly on the mutation sites subjected to examination. With this procedure, the elongation of complementary strands of the primers depends on the base species at the putative mutation sites.
   (2) A step, in which the synthetic reaction of complementary strands proceeds in small reaction vessels (subcells) that have been compartmentalized for each target gene and DNA sequence. The chemiluminescent reaction using pyrophosphate obtained during the complementary strand synthesis is also performed in the subcells.
   (3) A step, in which DNA is detected by photosensing this luminescence.

4. In the method according to 1, the method is characterized by the following step; a step, in which a group of the primers consists of the anchor primers having an arbitrary sequence that is not hybridized with the targets at the 5' terminus. The primers are designed so that mutation is located at the expected site when the 3'-terminal region is hybridized to the targets. Thus, the elongation of complementary strands of the primers is regulated by the presence of mutations.

5. In the method according to 4, the method is characterized by the following primers; a group of the primers that are hybridized with the samples are the anchor primers, in which the anchor sequences are varied to distinguish the correspondence between each primer and the target sequence and that between the 3' terminus of each primer and the DNA of a mutant or of a wild type.

6. In the method according to 1, the method is characterized by the following steps:
   (1) A step, in which a group of the first primers consists of the anchor primers having an arbitrary sequence at the 5' terminus, which are separately hybridized with all of the DNA subjected to examination to induce the complementary strand synthesis. After removing excess of the primers, the synthesis of complementary strands is performed by using the second anchor primers that contains the sequence complementary to a part of the synthesized first complementary strands and have been designed so that the 3' terminus is hybridized to the expected mutation sites.
   (2) A step, in which the DNA strands thus obtained are used for synthesis of complementary strands by using the primers that are hybridized with the anchor region of the anchor primers or their complementary strands. The copy number of the DNA strands is amplified by either PCR amplification, rolling-cycle amplification, or amplification utilizing a loop structure.

7. In the method according to either of 1 to 6, the method is characterized by the chemiluminescent detection; a group of the amplified DNA strands is degenerated to prepare single strands, which are captured by the DNA probes that can recognize the specific sequences and are immobilized to the subcells with the aid of the DNA sequences specific to the target species. The synthesis of complementary strands for each target is performed in each subcell, and pyrophosphate obtained during the synthesis is converted to ATP, which is then used for chemiluminescent reaction.

8. In the method according to either of 1 to 6, the method is characterized by the chemiluminescent detection; a group of the amplified DNA strands is degenerated to prepare single strands, and the DNA sequences specific to the target species are divided into different subcells. In the subcells are the probes previously maintained with matrix. The probe in each subcell contains the specific sequence that can recognize different targets. The synthesis of complementary strands for each target is performed in each subcell, and pyrophosphate obtained during the synthesis is converted to ATP, which is then used for chemiluminescent reaction.

9. In the method according to either of 1 to 8, the method is characterized by the chemiluminescent detection; using the anchor sequence regions containing the 3' terminus of the DNA strands captured by each subcell or their complementary strands as primer sequences, the synthesis of complementary strands is performed with the circular DNA added to the subcell as a template. Pyrophosphate obtained by this synthesis is converted to ATP, which is then used for chemiluminescent reaction.

10. In the method according to 9, the method is characterized by the following primers; the primers used for complementary strand synthesis in each subcell are common to at least several cells.

11. In the method according to either of 1 to 8, the method is characterized by the chemiluminescent detection; the anchor sequences containing the 3' terminus of the DNA strands captured in each subcell or their complementary strands is used as a primer to perform the synthesis of complementary strands with the DNA containing a loop sequence separately added as a template. Pyrophosphate obtained by this synthesis is converted to ATP, which is then used for chemiluminescent reaction.

12. In the method according to 9, the method is characterized by the following point; the capture of the DNA strands subjected to the complementary strand synthesis is achieved by the DNA probes immobilized to the solid surface of the subcell or to the surface of beads placed in the subcells.

13. In the method according to either of 1 to 12, the method is characterized by the following point; pyrophosphate used for detection is obtained by the synthesis of complementary DNA strands having the sequence that is not related to the target DNA subjected to the examination.

14. In the method according to 1, the method is characterized by the following step; the probes used for preparing the first complementary strands from a sample are the anchor primers, whose anchor region is self-hybridized to form a loop-like complementary strand, which acts as a template for the synthesis of the second complementary strands in the subcells using the second and the third primers. Pyrophosphate produced by formation of loop-like DNA strands in the synthesis of the second complementary strands is converted to ATP, which is consequently used for chemiluminescent reaction.

15. This method is the method for a DNA test and a genetic test, in which;
a group of probes consisting of multiple probe species is added to a sample subjected to examination, and two probes are hybridized with each of the different target sequence. The DNA probes are prepared so that the binding reaction of these probes in ligation reaction is affected by the presence of base mutations in the DNA subjected to examination. Using a group of the probes consisting of pairs of these probes, long DNA strands are prepared by ligation reaction. With these DNA strands or their complementary strands as a template, the synthesis of complementary strands is performed at least once in the subcells. Pyrophosphate, the product of the complementary strand synthesis, is converted to ATP and reacted with chemiluminescent substrates to develop luminescence in the subcells compartmentalized for each target. Mutations in genes or DNA are detected by monitoring the luminescence thus obtained.

16. In the method according to 15, the method is characterized by the following point; each of the paired primers used in ligation possesses the anchor sequence that is not hybridized with the target at either the 3' or 5' terminus. Using this sequence or its complementary sequence, the ligation products are PCR-amplified with the anchor sequence as a priming region. All the subject DNA sites are amplified simultaneously and used as a template for the synthetic reaction of complementary strands for the chemiluminescent detection.

17. In the method according to either 15 or 16, the method is characterized by the chemiluminescent detection; a group of the amplified DNA strands is degenerated to prepare single strands, which are captured by the DNA probes that can recognize different specific sequences and are immobilized to the subcells with the aid of the DNA sequences specific to the target species. The synthesis of complementary strands for each target is performed in each subcell, and pyrophosphate obtained during the synthesis is converted to ATP, which is then used for chemiluminescent reaction.

18. In the method according to either 15 or 16, the method is characterized by the chemiluminescent detection; a group of the amplified DNA strands is degenerated to prepare single strands, and the DNA sequences specific to the target species are divided into different subcells. In the subcells are the probes previously maintained with matrix. The probe in each subcell contains the specific sequence that can recognize different targets. The synthesis of complementary strands for each target is performed in each subcell, and pyrophosphate obtained during the synthesis is converted to ATP, which is then used for chemiluminescent reaction.

19. In the method according to either of 15 to 18, the method is characterized by the chemiluminescent detection; using the anchor sequences containing the 3' terminus of the DNA strands captured in each subcell or of their complementary strands as primers, the synthesis of complementary strands is performed with the circular DNA added to the subcell as a template. Pyrophosphate obtained by this synthesis is converted to ATP, which is then used for chemiluminescent reaction.

20. In the method according to 19, the method is characterized by the following primers; the primers used for complementary strand synthesis in each subcell are common to at least several cells.

21. In the method according to either of 15 to 18, the method is characterized by the chemiluminescent detection; the anchor sequences containing 3'-terminal region of the DNA strands captured in the subcells or their complementary strands are used as a primer to perform synthesis of complementary strands using the DNA with a loop structure separately added as a template. Pyrophosphate obtained by this synthesis is converted to ATP, which is then used for chemiluminescent reaction.

22. In the method according to 19, the method is characterized by the following point; the capture of the DNA strands subjected to the complementary strands synthesis is achieved by the DNA probes immobilized to the solid surface of the subcell or to the surface of beads placed in the subcells.

23. In the method according to either of 15 to 22, the method is characterized by the following point; pyrophosphate used for detection is obtained by the synthesis of complementary DNA strands having the sequence that is not related to the target DNA subjected to the examination.

24. In the method according to 15, the method is characterized by the following step; a group of pairs of the probes used for preparing the ligation product from a sample are the anchor primers, whose anchor region is self-hybridized and forms a loop-like complementary strand, which acts as a template for the synthesis of complementary strands in the subcells using the third primers. Pyrophosphate produced by formation of loop-like DNA strands in the synthesis of complementary strands is converted to ATP, which is consequently used for chemiluminescent reaction.

25. This method is the method for detecting mutations of base species occurring in DNA base sequences, which is characterized by the following point; the primers with a common sequence at their 5' termini can regulate the reaction of complementary strand synthesis, where the target DNA strands are used as a template, depending on the presence or absence of mutations. Following the synthesis of complementary strands using these primers, pyrophosphate is produced during the synthesis of complementary DNA strands using these copied DNA strands or their complementary strands as templates. Pyrophosphate is converted to ATP, which is subsequently used for the chemiluminescent reaction. The presence of DNA mutations or the presence of target DNA is determined by luminescent intensity.

26. This method is the method for detecting specific sequences and mutations in DNA base sequences, which is characterized by the following steps involving genomes or multiple target DNA as a template:
(1) Multiple species of the first DNA probes (primers) are hybridized in a single reaction vessel to prepare multiple species of the first complementary strands by the synthesis of complementary strands.
(2) Excess of the first probes are isolated and removed from the synthesized complementary strands.
(3) With the first complementary strands as a template, the second synthesis of complementary strands is performed using multiple species of the second probes to obtain the second complementary strands, which partially contains the same sequence as that of the original DNA.

(4) In each compartmentalized area sorted with species of the complementary strands, pyrophosphate is produced in the synthesis of the second complementary strands or in the complementary strand synthesis using the second complementary strands as a template, and is converted to ATP, which develops chemiluminescence for detection.

According to this invention, the DNA fragments containing many sites subjected to a DNA test are extracted en bloc and amplified if necessary. Following these processes, the presence of mutations is easily examined by whether synthesis of complementary strands is initiated or not. The invention provides a method for a low-cost DNA test by making use of chemiluminescence, which doe not require expensive reagents or equipment. The invention also discloses a method, in which amplification of the copy number of targets by PCR and other techniques is not necessary; instead of amplification of the copy number of targets, the amount of pyrophosphate produced in synthesis of complementary strands is amplified for easier detection, which makes the detection sensitivity much higher.

It should be further understood by those skilled in the art that the foregoing description has been made on embodiments of the invention and that various changes and modifications may be made in the invention without departing from the spirit of the invention and the scope of the appended claims.

What is claimed is:

1. A method for examining nucleotide sequences which comprises:
   (1) adding a group of primers consisting of multiple primer species to a solution containing a sample of nucleic acid subjected to examination, and performing simultaneous synthesis of complementary strands at each of the multiple regions of the nucleic acid containing target nucleotide sequences to be examined;
   (2) designing DNA probes with specific sequences so that elongation of complementary strands is affected by the presence or absence of mutations in said target nucleotide sequences wherein the same number of such DNA probes and said target sequences is used for elongation of complementary strands;
   (3) immobilizing said DNA probes in subcells of a reaction vessel that are compartmentalized for each said DNA probe;
   (4) adding the solution obtained after step (1) to the reaction vessel, wherein said DNA probes are allowed to hybridize with said target sequences or sequences complementary to said target sequences under condition that the solution can freely move among said subcells, and then the excess amount of the solution is removed so that the remaining solution can no longer freely move among said subcells;
   (5) performing elongation reaction of complementary strands using said target sequences or the sequences complementary to said target sequences as a template and the following reaction, in which pyrophosphate produced during said elongation reaction is converted to ATP and reacted with chemiluminescent substrates to develop luminescence, in the subcells of the reaction vessel, wherein elongation of complementary strand occurs for the nucleic acid whose sequences are complementary to said probes; and
   (6) determining the presence or absence of mutations in said target nucleotide sequences based upon said luminescence.

2. A method for examining nucleotide sequences according to claim 1, wherein the step (1) comprises:
   (a) adding first anchor primers each having a first anchor sequence at the 5' terminus that is not hybridized with said targets;
   (b) removing excess of said first anchor primers after said synthesis of complementary strands, followed by using second anchor primers for synthesis of complementary strands
   these second anchor primers containing a second anchor sequence at the 5' terminus that is not hybridized with said targets and a sequence complementary to a part of the complementary strands in (1) (b);
   (c) preparing DNA strands with said first or second anchor sequence at least at one terminus by using these second anchor primers; and
   (d) amplifying the number of copies of said DNA strands with said first or second anchor sequence as a priming region.

3. A method for examining nucleotide sequences according to claim 1
   wherein in step (2), said DNA probes are designed so that the base at 3' terminus of said DNA probes is located exactly at a mutation site in said target nucleotide sequences; and
   the elongation of complementary strands depends on the base species at the mutation site.

4. A method for examining nucleotide sequences according to claim 1 wherein the group of said primers consists of the anchor primers having an arbitrary sequence, defining a 3' terminal region, and each of the anchor primers is designed so that it has a base at the expected site for recognizing a mutation site in said targets; and the elongation of complementary strands is dependent on the presence of mutation in said targets.

5. A method for examining nucleotide sequences according to claim 4 in which sequences of said anchor primers are varied so so as to provide complementarity between the 3'-terminal region and the DNA of a mutant or a wild type.

6. A method for examining nucleotide sequences according to claim 2 in which the copy number of DNA strands is amplified by either PCR amplification, rolling-cycle amplification or amplification using a loop structure.

7. A method for examining nucleotide sequences according to claim 1, in which said DNA probes contain the sequences specific to said target sequences and are immobilized onto the surface of said subcells, and said amplified DNA strands are denatured to prepare single strands, which are captured in said subcells by hybridization between this single-strand DNA and said DNA probes.

8. A method for examining nucleotide sequences according to claim 2 in which said DNA probes contain the sequences specific to said target nucleotide sequences and are maintained with matrix in said subcells, and said amplified DNA strands are denatured to prepare single strands, which are captured in said subcells by hybridization between this single-strand DNA and said DNA probes.

9. A method for examining nucleotide sequences according to claim 2 in which said DNA probes contain the sequences specific to said target nucleotide sequences and are maintained in said subcells, said amplified DNA strands are denatured to prepare single strands, which are captured in said subcells by hybridization between this single-strand DNA and said DNA probes, and synthesis of complementary strands is performed with circular DNA added to said subcell as a template and by using the anchor sequence containing the 3' terminus of said single-strand DNA thus captured or of their complementary strands as a primer sequence.

10. A method for examining nucleotide sequences according to claim 9 in which the primers used for synthesis of complementary strands in each of said subcells are common to said multiple subcells.

11. A method for examining nucleotide sequences according to claim 2 in which the anchor sequence containing the 3'-terminal region of said DNA strands captured in said subcells or their complementary strands is used as a primer to perform synthesis of complementary strands using DNA with a loop structure separately added as a template.

12. A method for examining nucleotide sequences according to claim 9 in which the capture of DNA strands subjected to complementary strand synthesis is achieved by binding of said DNA strands to said DNA probes immobilized to the solid surface of said subcells or to the surface of beads placed in said subcells.

13. A method for examining nucleotide sequences according to claim 2 in which pyrophosphate is produced during synthesis of complementary strands using the DNA strands.

14. A method for examining nucleotide sequences according to claim 1 in which the probes used for preparing the first complementary strands from the sample are the first anchor primers, whose anchor region is self-hybridized to form a loop-like complementary strand, which acts as templates for the second synthesis of complementary strands in said subcells by using second anchor primers and the third primers, and pyrophosphate produced by formation of loop-like DNA strands in said second synthesis of complementary strands is converted to ATP, which is consequently utilized for chemiluminescent reaction.

15. A method for examining nucleotide sequences characterized by detection of specific sequences and mutations in base sequences of target DNA, and the method, using a solution having genomes or multiple target DNA to provide templates, comprising:

(1) hybridizing multiple species of first probes to said templates in a single reaction vessel and preparing multiple species of first complementary strands by the first synthesis of complementary strands, wherein the first probes are immobilized in subcells of a reaction vessel that are compartmentalized for each of said probes, wherein said probes are allowed to hybridize with said target DNA under condition that the solution can freely move among said subcells; and then the excess amount of the solution is removed so that the solution can no longer freely move among said subcells;

(2) isolating and removing excess of the first probes from said first complementary strands;

(3) with said first complementary strands as a template, performing the second synthesis of complementary strands using multiple species of second probes to obtain second complementary strands, which partially contains the same sequence as that of said target DNA whereby, in each compartmentalized area sorted with species of said first complementary strands, pyrophosphate is produced in the synthesis of said second complementary strands or in the complementary strand synthesis using said second complementary strands as a template, and is convened to ATP, which develops chemiluminescence for detection.

16. A method of examining nucleotide sequences which comprises:

(1) providing a reaction vessel wherein a first probe consisting essentially of a first nucleotide sequence is immobilized in a first subcell of the reaction vessel, a second probe consisting essentially of a second nucleotide sequence different from the first nucleotide sequence is immobilized in a second subcell of the reaction vessel, and the first and second subcells are compartmentalized for each other;

(2) adding to the reaction vessel a solution containing a target nucleotide sequence in such a way that said solution can freely move between said first and second subcells, whereby the target nucleotide sequence hybridizes with said first or second probe;

(3) removing the excess amount of the solution so that remaining solution can no longer move between said first and second subcells;

(4) adding to the first and second subcells, reaction solutions necessary for complementary strand synthesis so that elongation reaction of the first probe or second probe is performed using said hybridized target nucleotide sequence as a template, and pyrophosphate produced during said elongation reaction is converted to ATP and reacted with chemiluminescent substrate to develop luminescence; and (5) detecting said luminescence to detect a specific sequence in the target nucleotide sequence.

17. A method for examining nucleotide sequence according to claim 16, wherein said first and second probes are for detecting wild-type or mutated target nucleotide sequence.

* * * * *